(12) United States Patent
Russell et al.

(10) Patent No.: US 6,235,515 B1
(45) Date of Patent: May 22, 2001

(54) MALATHION CARBOXYLESTERASE

(75) Inventors: Robyn Joyce Russell, Wanniassa; Richard David Newcomb, Mt Albert; Peter Malcolm Campbell, Cook; Geoffrey Charles de Quetteville Robin, Aranda; Charles Claudianos, Isabella Plains, all of (AU); Kerrie-Ann Smyth; Thomas Mark Boyce, both of Syracuse, NY (US); John Graham Oakeshott, Wanniassa; Jeremy Colin Brownlie, Via Queanbeyan, both of (AU)

(73) Assignee: The Commonwealth Scientific and Industrial Research Organization, Australian Capital Territory (AU)

( * ) Notice: Subject to any disclaimer, the term of this patent is extended or adjusted under 35 U.S.C. 154(b) by 0 days.

(21) Appl. No.: 09/068,960

(22) PCT Filed: Nov. 22, 1996

(86) PCT No.: PCT/AU96/00746

§ 371 Date: May 20, 1998

§ 102(e) Date: May 20, 1998

(87) PCT Pub. No.: WO97/19176

PCT Pub. Date: May 29, 1997

(30) Foreign Application Priority Data

Nov. 23, 1995 (AU) .................................................. PN6751

(51) Int. Cl.[7] .............................. C12P 21/06; C12N 9/00; C12N 9/18; C12N 1/20; C12N 15/00
(52) U.S. Cl. ......................... 435/197; 435/183; 435/69.1; 435/252.3; 435/320.1; 536/23.2
(58) Field of Search .................................... 435/197, 252.3, 435/320.1, 71.1, 262, 262.5; 536/23.2; 530/350

(56) References Cited

FOREIGN PATENT DOCUMENTS

| 14502/95 | 7/1995 | (AU). |
| WO9519440-A1 | * 7/1995 | (WO). |

OTHER PUBLICATIONS

Biochemical Genetics, vol. 32, Nos 1/2, 1994 p. 9–24 (S Whyard et al.,) "Insecticide Resistance and Malathion Carboxylesterase in the Sheep Blowfly, *Lucitia Cuprina*".

Pesticide Biochemistry and Physiology vol. 50, No. 3, (1994) p. 198–206 (S Whyard and V K Walker) "Characterization of Malathion Carboxylesterase in the Sheep Blowfly *Lucilia Cuprina*".

Archives of Insect Biochemistry and Physiology vol. 29, (1995) p. 329–342 (S Whyard et al.,) "Characterization of a Novel Esterase conferring Insecticide Resistance in the Mosquito *Culex tarsalis*".

Insect Biochem Molec Biol vol. 24, No. 8, (1994) p. 819–827 (S Whyard et al.,) "Isolation of an Esterase Conferring Insecticide Resistance in the Mosquito *Culex tarsalis*".

* cited by examiner

Primary Examiner—Rebecca E. Prouty
Assistant Examiner—Manjunath N. Rao
(74) Attorney, Agent, or Firm—McDermott, Will & Emery

(57) ABSTRACT

The present invention provides an isolated DNA molecule encoding Malathion Carboxylesterase capable of hydrolysing at least one organophosphate selected from the group consisting of carboxylester organophosphates and dimethyloxon organophosphates. The DNA molecule comprises a nucleotide sequence having at least 60%, preferably at least 80% and more preferably at least 95% homology with $Lc\alpha E_7$, in which the protein encoded by the DNA molecule differs from $E_3$ at least in the substitution of Trip at position 251 with an amino acid selected from the group consisting of Leu, Ser, Ala, Ile, Val, Thr, Cys, Met and Gly. The preferred substituents are Leu and Ser.

9 Claims, 16 Drawing Sheets

FIG. 1A

| SEQ ID NO:8  | Lc743   |
| SEQ ID NO:10 | Rm8con  |

| SEQ ID NO:7 | Lc743  |
| SEQ ID NO:1 | RM8A   |
| SEQ ID NO:3 | RM8B   |
| SEQ ID NO:5 | RM8C   |
| SEQ ID NO:9 | Rm8con |

```
                 M   N   F   N   V   S   L   M   E   K   L   K   W   K   I   K   C   I   E   N           20
Lc743    1   ATGAATTTCAACGTTAGTTTGATGGAGAAATTAAAATGGAAGATTAAATGCATTGAAAAT    60
             ---------+---------+---------+---------+---------+---------+
                      Lc743/5'
Rm8con       ............................................................
RM8A         ............................................................
RM8B         ............................................................
RM8C         ............................................................

K   E   L   N   Y   R   L   T   T   N   E   T   V   A   E   T   E   Y   G          40
Lc743   61   AAGTTTTTAAAACTATCGTTTAACTACCAATGAAACGGGTAGCTGAAACTGAATATGGC  120
             ---------+---------+---------+---------+---------+---------+
Rm8con       ............................................................
RM8A         ............................................................
RM8B         ............................................................
RM8C         ............................................................

K   V   K   G   V   K   R   L   T   V   Y   D   D   S   Y   Y   S   F   E   G       60
Lc743  121   AAAGTGAAAGGCGTTAAACGTTTAACTGTGTACGATGATTCCTACTACAGTTTTGAGGGT  180
             ---------+---------+---------+---------+---------+---------+
Rm8con       ............................................................
RM8A         ............................................................
RM8B         ............................................................
RM8C         ............................................................

I   P   Y   A   Q   P   P   V   G   E   L   R   F   K   A   P   Q   R   P   T      80
Lc743  181   ATACCGTACGCCCAACCGCCAGTGGGTGAGCTGAGATTTAAACGACCCCAGCGACCAACA  240
             ---------+---------+---------+---------+---------+---------+
Rm8con       ............................................................
RM8A         ............................................................
RM8B         ............................................................
RM8C         ............................................................
```

FIG. 1B

```
        I    N    I    Q    Y    R    L    G    A    L    G    F    L    S    L    N    S    E    D    L      180
Lc743   .    .    .    .    .    .    .    .    .    .    .    .    .    .    .    .    .    .    .    .
Rm8con  ---------+---------+---------+---------+---------+---------+                                          540
   481  ATTAACATACAATATCGTTGGGAGCTCTAGGTTTTCTAAGTTTAAATTCAGAAGACCTT
RM8A    . . . . . . . . . . . . . . . . . . . . . . . . . . . . . .
RM8B    . . . . . . . . . . . . . . . . . . . . . . . . . . . . . .
RM8C    . . . . . . . . . . . . . . . . . . . . . . . . . . . . . .
RM8con  . . . . . . . . . . . . . . . . . . . . . . . . . . . . . .

N    V    P    G    N    A    G    L    K    D    Q    V    M    A    L    R    W    I    K    N      200
Lc743   .    .    .    .    .    .    .    .    .    .    .    .    .    .    .    .    .    .    .    .
Rm8con  ---------+---------+---------+---------+---------+---------+                                          600
   541  AATGTGCCCGGTAATGCGGGCCTTAAAGATCAAGTCATGGCCCTTGCGTTGGATTAAAAAT
RM8A    . . . . . . . . . . . . . . . . . . . . . . . . . . . . . .
RM8B    . . . . . . . . . . . . . . . . . . . . . . . . . . . . . .
RM8C    . . . . . . . . . . . . . . . . . . . . . . . . . . . . . .
RM8con  . . . . . . . . . . . . . . . . . . . . . . . . . . . . . .

N    C    A    N    F    G    G    N    P    D    N    I    T    V    F    G    E    S    A    G      220
Lc743   .    .    .    .    .    .    .    .    .    .    .    .    .    .    .    .    .    .    .    .
Rm8con  ---------+---------+---------+---------+---------+---------+                                          660
   601  AATTGCGCCAACTTTGGTGGCAATCCCGATAATATTACAGTCTTTGGTGAAAGTGCCGGT
RM8A    . . . . . . . . . . . . . . . . . . . . . . . . . . . . . .
RM8B    . . . . . . . . . . . . . . . . . . . . . . . . . . . . . .
RM8C    . . . . . . . . . . . . . . . . . . . . . . . . . . . . . .
RM8con  . . . . . . . . . . . . . . . . . . . . . . . . . . . . . .

A    A    S    T    H    U    M    M    L    T    E    Q    T    R    G    L    F    H    R    G      240
Lc743   .    .    .    .    .    .    .    .    .    .    .    .    .    .    .    .    .    .    .    .
Rm8con  ---------+---------+---------+---------+---------+---------+                                          720
   661  GCTGCCTCTACCCACCACTACATGATGTTAACCGAACAAACTCGGCGGTCTTTTCCATCGTGGT
RM8A    . . . . . . . . . . . . . . . . . . . . . . . . . . . . . .
RM8B    . . . . . . . . . . . . . . . . . . . . . . . . . . . . . .
RM8C    . . . . . . . . . . . . . . . . . . . . . . . . . . . . . .
RM8con  . . . . . . . . . . . . . . . . . . . . . . . . . . . . . .
```

```
              H   V   T   G   E   T   P   T   A   D   N   F   M   D   L   C   S   H   I   Y       420
Lc743         .   .   .   .   .   .   .   .   .   .   N   .   .   .   .   .   .   .   .   .
Rm8con  1201  ---|---|---|---|---|---|---|---|---|---|-L-|---|---|---|---|---|---|---|---|---|+   1260
              CATGTTACAGGAGAAACACCAACAGCTGATAATTTTATGGATCTTTGCTCTCACATCTAT
RM8A          . . . . . . . . . . . . . . . . . . . .
RM8B          . . . . . . . . . . . . . . . . . . . .
RM8C          . . . . . . . . . . . . . . . . . . . .
Rm8con        . . . . . . . . . . . . . . . . . . . .

F   W   F   P   M   H   R   L   L   Q   L   R   F   N   H   T   S   G   T   P       440
Lc743         .   .   .   .   .   .   .   .   .   .   .   .   .   .   .   .   .   .   .   .
Rm8con  1261  ---|---|---|---|---|---|---|---|---|---|---|---|---|---|---|---|---|---|---|---|+  1320
              TTCTGGTTCCCCATGCATCGTTTGTTGCAATTACGTTTCAATCACACCTCCGGTACACCC
RM8A          . . . . . . . . . . . . . . . . . . . .
RM8B          . . . . . . . . . . . . . . . . . . . .
RM8C          . . . . . . . . . . . . . . . . . . . .
Rm8con        . . . . . . . . . . . . . . . . . . . .

V   Y   L   Y   R   F   D   F   D   S   E   D   L   I   N   P   Y   R   I   M       460
Lc743         .   .   .   .   .   .   .   .   .   .   .   .   .   .   .   .   .   .   .   .
Rm8con  1321  ---|---|---|---|---|---|---|---|---|---|---|---|---|---|---|---|---|---|---|---|+  1380
              GTCTACTTGTATCGCTTTGACTTTGATTCGGAAGATCTTATTAATCCCTATCGTATTATG
RM8A          . . . . . . . C . . . . . . . . . . . .
RM8B          . . . . . . . C . . . . . . . . . . . .
RM8C          . . . . . . . C . . . . . . . . . . . .
Rm8con        . . . . . . . C . . . . . . . . . . . .

R   S   G   R   G   V   K   G   V   S   H   A   D   E   L   T   Y   F   F   W       480
Lc743         .   .   .   .   .   .   .   .   .   .   .   .   .   .   .   .   .   .   .   .
Rm8con  1381  ---|---|---|---|---|---|---|---|---|---|---|---|---|---|---|---|---|---|---|---|+  1440
              CGTAGTGGACGTGGGTGTGTTAAGGGTGTTAGTCATGCTGATGAATTAACCTATTTCTTCTGG
RM8A          . . . . . . . . . . . . . . . . . . . .
RM8B          . . . . . . . . . . . . . . . . . . . .
RM8C          . . . . . . . . . . . . . . . . . . . .
Rm8con        . . . . . . . . . . . . . . . . . . . .
```

FIG. 1F

```
                   N   Q    L   A   K   R   M   P   K   E   S   R   E   Y   K   T   I   E   R   M       500
Lc743         ---------+---------+---------+---------+---------+---------+
Rm8con   1441 AATCAATTGGCCAAACGTATGCCTAAAGAATCGCGTGAATACAAAACAATTGAACGTATG       1500
RM8A          ............................................................
RM8B          ............................................................
RM8C          ..................L.........................................
Rm8con        ............................................................

T   G   I   W   I   Q   F   A   T   T   G   N   P   Y   S   N   E   I   E   G       520
Lc743         ---------+---------+---------+---------+---------+---------+
Rm8con   1501 ACTGGTATATGGATACAATTTGCCACCACTGGTAATCCTTATAGCAATGAAATTGAAGGT       1560
RM8A          ............................................................
RM8B          ............................................................
RM8C          ............................................................
Rm8con        ............................................................

M   E   N   V   S   W   D   P   I   K   K   S   D   E   V   Y   K   C   L   N       540
Lc743         ---------+---------+---------+---------+---------+---------+
Rm8con   1561 ATGGAAAATGTTTCCTGGGATCCAATTAAGAAATCCGACGAAGTATACAAGTGTTTGAAT       1620
RM8A          .....................................T.T..T................
RM8B          .....................................T.T..T................
RM8C          .....................................T.T..T................
Rm8con        ............................................................

I   S   D   E   L   K   M   I   D   V   P   E   M   D   K   I   K   Q   W   E       560
Lc743         ---------+---------+---------+---------+---------+---------+
Rm8con   1621 ATTAGTGACGAATTGAAAATGATTGATGTGCCTGAAATGGATAAGATTAAACAATGGGAA       1680
RM8A          .........................T.T...............................G
RM8B          .........................T.T...............................G
RM8C          ............................................................G
Rm8con        ............................................................G
```

FIG. 1G

```
                    S   M   E   E   K   H   R   D   L   E   *
Lc743
Rm8con  1681    ----:----|----:----|----:----|----:----|----:----|  570
Lc743           TCGATGTTTGAAAAACATAGAGATTTATTTTAG                    1713
RM8A            ................................
RM8B            ................................
RM8C            ................................
Rm8con          ................................
                         Lc743/3'
```

FIG. 1H

| | | | |
|---|---|---|---|
| SEQ ID NO:13 MdαE7 | 1 | MTFLKQFIFRLKLCVKCMVNKYTNYRLSTNETQIIDTEYGQIKGVKRMTV | 50 |
| SEQ ID NO:8 LcαE7 | 1 | MNFNVSLMEKLKWKIKCIENKFLNYRLTTNETVVAETEYGKVKRLTV | 50 |
| | 51 | YDDSYYSFESIPYAKPPVGELRFKAPQUPVPWEGVRDCCGPANRSVQTDF | 100 |
| | 51 | YDDSYYSFEGIPYAQPPVGELRFKAPQRPTPWDGVRDCCNHKDKSVQVDF | 100 |
| | 101 | ISGKPTGSEDCLYLNVYTNDLNPDKRRPVMFIHGGDFIFGEANRWFGP | 150 |
| | 101 | ITGKVCGSEDCLYLSVYTNNLNPETKRPVLVYIHGGGFIIGENHRDMYGP | 150 |
| | 151 | DYFMKKPVVLVTVQYRLGVLGFLSLKSENLNVPGNAGLKDQVMALRWVKS | 200 |
| | 151 | DYFIKKDVVLINIQYRLGALGFLSLNSEDLNVPGNAGLKDQVMALRWIKN | 200 |
| | 201 | NIAIFGGDVDNITVFGESAGGASTHYMMITEQTRGLFHRGIMMSGNSMCS | 250 |
| | 201 | NCANFGGNPDNITVFGESAGAASTHYMMLTEQTRGLFHRGILMSGNAICP | 250 |
| | 251 | WASTECQSRALTMAKRVGYKGEDNEKDILEFLMKANPYDLIKEEPQVLTP | 300 |
| | 251 | WANTQCQHRAFTLAKLAGYKGEDNDKDVLEFLMKAKPQDLIKLEEKVLTL | 300 |
| | 301 | ERMQNKVMFPFGPTVEPYQTADCVVPKPIREMVKSAWGNSIPTLIGNTSY | 350 |
| | 301 | EERTNKVMFPFGPTVEPYQTAKCVLPKHPREMVKTAWGNSIPTMMGNTSY | 350 |
| | 351 | EGLLSKSVAKQYPEVVKELESCVNYVPWELADSERSAPETLERAAIVKKA | 400 |
| | 351 | EGLFFTSILKQMPMLVKELETCVNFVPSELADAERTAPETLEMGAKIKKA | 400 |

FIG. 2A

```
401 HVDGETPTLDNFMELCSYFYFLFPMHRFLQLRFNHTAGTPIYLYREDFDS  450
401 HVTGETPTADNFMDLCSHIYFWFPMHRLLQLRFNHTSGTPVYLYREDFDS  450
451 EEIINPYRIMRFGRGVKGVSHADELTYLFWNILSKRLPKESREYKTIERM  500
451 EDLINPYRIMRSGRGVKGVSHADELTYFFWNQLAKRMPKESREYKTIERM  500
501 VGIWTEFATTGKPYSNDIAGMENLTWDPIKKSDDVYKCLNIGDELKVMDS  550
501 TGIWIQFATTGNPYSNEIEGMENVSWDPIKKSDEVYKCLNISDELKMIDV  550
551 PEMDKIKQGASIFDKKKELF  570
551 PEMDKIKQWESMFEKHRDLF  570
```

FIG. 2B

SEQ ID NO:14

SEQ ID NO:13

```
      ATGACTTTTCTGAAGCAATTCATATTTCGCCTGAAACTATGCTTTAAATGCATGGTCAAT
   1  ------------------------------------------------------------  60
      TACTGAAAAGACTTCGTTAAGTATAAAGCGGACTTTGATACGAAATTTACGTACCAGTTA

M  T  F  L  K  Q  F  I  F  R  L  K  L  C  F  K  C  M  V  N  -

AAATACACAAACTACCGTCTGAGTACAAATGAAACCCAAATAATCGATACTGAATATGGA
  61  ------------------------------------------------------------ 120
      TTTATGTGTTTGATGGCAGACTCATGTTTACTTTGGGTTTATTAGCTATGACTTATACCT

K  Y  T  N  Y  R  L  S  T  N  E  T  Q  I  D  T  E  Y  G  -

CAAATTAAGGGTGTTAAGCGAATGACCGTCTACGATGATTCTTACTACAGTTTCGAGAGT
 121  ------------------------------------------------------------ 180
      GTTTAATTCCCACAATTCGCTTACTGGCAGATGCTACTAAGAATGATGTCAAAGCTCTCA

Q  I  K  G  V  K  R  M  T  V  Y  D  D  S  Y  S  F  E  S  -

ATACCCTATGCTAAGCCCTCCAGTGGGTGAGTTGAGATTCAAGGCACCCCAGCGGCCTGTA
 181  ------------------------------------------------------------ 240
      TATGGGATACGATTCGGGAGGTCACCCACTCTAAGTTCCGTGGGGTCGCCGGACAT

I  P  Y  A  K  P  P  V  G  E  L  R  F  K  A  P  Q  R  P  V  -

CCATGGGAGGGTGTACGTGATTGCTGTGGGCCAACAGATCGGTACAGACAGATTTC
 241  ------------------------------------------------------------ 300
      GGTACCCTCCCACATGCACTAACGACACTGGTTGTCTAGCCATGTCTGTCTAAAG

P  W  E  G  V  R  D  C  C  G  P  A  N  R  S  V  Q  T  D  F  -

ATAAGTGGCAAACCCACAGGTTCGGAGGATTGTCTATACCTGAATGTGTATACCAATGAC
 301  ------------------------------------------------------------ 360
      TATTCACCGTTTGGGTGTCCAAGCCTCCTAACAGATATGGACTTACACATATGGTTACTG

I  S  G  K  P  T  G  S  E  D  C  L  Y  L  N  V  Y  T  N  D  -
```

FIG. 3A

```
361  TTGAACCCAGACAAAAGGCGTCCTGTTATGGTTTTCATCCATGGCGGAGATTTTATTTTC  420
     ----+----|----+----|----+----|----+----|----+----|----+----|
     AACTTGGGTCTGTTTTCCGCAGGACAATACCAAAAGTAGGTACCGCCTCTAAAATAAAAG

L   N   P   D   K   R   R   P   V   M   V   F   I   H   G   G   D   F   I   F

421  GGCGAAGCAAATCGTAACTGGTTTGGTCCCGACTACTTTATGAAGAAACCCGTGGTCTTG  480
     ----+----|----+----|----+----|----+----|----+----|----+----|
     CCGCTTCGTTTAGCATTGACCAAACCAGGGCTGATGAAATACTTCTTTGGGCACCAGAAC

G   E   A   N   R   N   W   F   G   P   D   Y   F   M   K   K   P   V   V   L

481  GTAACCGTGCAATATCGTTTGGGTGTGTTGGGTTTCCTTAGCCTGAAATCGGAAAATCTC  540
     ----+----|----+----|----+----|----+----|----+----|----+----|
     CATTGGCACGTTATAGCAAACCCACACAACCCAAAGGAATCGGACTTTAGCCTTTTAGAG

V   T   V   Q   Y   R   L   G   V   L   G   F   L   S   L   K   S   E   N   L

541  AATGTCCCCGGCAACGCTGGCCTCAAGGATCAAGTAATGGCCTTGAGATGGGTCAAGAGT  600
     ----+----|----+----|----+----|----+----|----+----|----+----|
     TTACAGGGGCCGTTGCGACCGGAGTTCCTAGTTCATTACCGGAACTCTACCCAGTTCTCA

N   V   P   G   N   A   G   L   K   D   Q   V   M   A   L   R   W   V   K   S

601  AATATTGCCATTTTCGGTGGCGATGTAGACAATATTACCGTCTCTTCCGGCGAAAGTGCTGGT  660
     ----+----|----+----|----+----|----+----|----+----|----+----|
     TTATAACGGTAAAAGCCACCGCTACATCTGTTATAATGGCAGAAGCCGCTTTCACGACCA

N   I   A   I   F   G   G   D   V   D   N   I   T   V   F   G   E   S   A   G

661  GGGGCCTCAAACCCATTACATGATGATAACCGAACAGACCCGTGGTTTATTCCATCGTGGT  720
     ----+----|----+----|----+----|----+----|----+----|----+----|
     CCCCGGAGTTGGGTAATGTACTACTATTGGCTTGTCTGGGCACCAAATAAGGTAGCACCA

G   A   S   T   H   Y   M   M   I   T   E   Q   T   R   G   L   F   H   R   G
```

FIG. 3B

```
      ATCATGATGTCCGGTAATTCCATGTGCTCTCATGGGCCTCTACAGAATGCCAAAGTCGTGCG
721   ------------+---------+---------+---------+---------+---------+  780
      TAGTACTACAGGCCATTAAGGTACACGAGTACCCGGAGATGTCTTACGGTTTCAGCACGC

I  M  M  S  G  N  S  M  C  S  W  A  S  T  E  C  Q  S  R  A

CTCACCATGGCCAAACGTGTTGGCTATAAGGGAGAGGACAATGAAAAAGATATCCTGGAA
781   ------------+---------+---------+---------+---------+---------+  840
      GAGTGGTACCGGTTTGCACAACCGATATTCCCTCTCCTGTTACTTTTTCTATAGGACCTT

L  T  M  A  K  R  V  G  Y  K  G  E  D  N  E  K  D  I  L  E

TTCCTAATGAAAGCCAATCCCTATGATTTGATCAAAGAGGAGCCACAAGTTTTGACACCC
841   ------------+---------+---------+---------+---------+---------+  900
      AAGGATTACTTTCGGTTAGGGATACTAAACTAGTTTCTCCTCGGTGTTCAAAACTGTGGG

F  L  M  K  A  N  P  Y  D  L  I  K  E  P  Q  V  L  T  P

GAAAGAATGCAAAATAAGGTCATGTTTCCTTTTGGACCCACTGTAGAACCATACCAGACA
901   ------------+---------+---------+---------+---------+---------+  960
      CTTTCTTACGTTTTATTCCAGTACAAAGGAAAACCTGGGTGACATCTTGGTATGGTCTGT

E  R  M  Q  N  K  V  M  F  P  F  G  P  T  V  E  P  Y  Q  T

GCCGACTGTGTGTACCCCAAACCAATCAGAGAAATGGTGAAGAGCGCCTGGGGAAATTCG
961   ------------+---------+---------+---------+---------+---------+  1020
      CGGCTGACACACATGGGGTTTGGTTAGTCTCTTTACCACTTCTCGCGGACCCCTTTAAGC

A  D  C  V  P  K  P  I  R  E  M  V  K  S  A  W  G  N  S

ATACCCACATTGATAGGCAATACCTCCTACGAAGGTTTGCTTTCCAAATCAATTGCCAAA
1021  ------------+---------+---------+---------+---------+---------+  1080
      TATGGGTGTAACTATCCGTTATGGAGGATGCTTCCAAACGAAAAGTTTAGTTAACGGTTT

I  P  T  L  I  G  N  T  S  Y  E  G  L  L  S  K  S  I  A  K
```

FIG. 3C

```
      CAATATCCGGAGGTTGTAAAAGAGTTGGAATCCTGTGTGAATTATGTGCCTTGGGAGTTG
1081  ------+---------+---------+---------+---------+---------+ 1140
      GTTATAGGCCTCCAACATTTTCTCAACCTTAGGACACACTTAATACACGGAACCCTCAAC

Q  Y  P  E  V  K  E  L  E  S  C  V  N  Y  V  P  W  E  L

GCTGACAGTGAACGCCAGTGCCCCGGAAACCCTGGAGAGGGCTGCCATTGTGAAAAAGGCC
1141  ------+---------+---------+---------+---------+---------+ 1200
      CGACTGTCACTTGCGGTCACGGGGCCTTTGGACCCTCCCGACGGTAACACTTTTTCCGG

A  D  S  E  R  S  A  P  E  T  L  E  R  A  A  I  V  K  K  A

CATGTGGATGGGGAAACACCTACTCTGGATAATTTTATGGAGCTTTGCTCCTATTCTAT
1201  ------+---------+---------+---------+---------+---------+ 1260
      GTACACCTACCCCTTTGTGGATGAGACCTATTAAAATACCTCGAAACGAGGATAAAGATA

H  V  D  G  E  T  P  T  L  D  N  F  M  E  L  C  S  Y  F  Y

TTCCTCTTCCCCATGCATCGCTTCAACAATTGCGCTTCAACCACACAGCTGGCACTCCC
1261  ------+---------+---------+---------+---------+---------+ 1320
      AAGGAGAAGGGGTACGTAGCGAAGTTGTTAACGCGAAGTTGGTGTGTCGACCGTGAGGG

F  L  F  P  M  H  R  F  L  Q  L  R  E  N  H  T  A  G  T  P

ATTTATTGTATCGTTTCGATTCCGAAGAAATTATTAACCCCTATCGTATTATG
1321  ------+---------+---------+---------+---------+---------+ 1380
      TAAATAAACATAGCAAAGCTAAGGCTTCTTTTAATAATTGGGATAGCATAATAC

I  Y  L  Y  R  F  D  F  D  S  E  E  I  I  N  P  Y  R  I  M

CGTTTTGGCCGTGGCGTTAAAGGTGTGTAAGCCATGCCGATGAGCTAACCTATCTCTTCTGG
1381  ------+---------+---------+---------+---------+---------+ 1440
      GCAAAACCGGCACCGCAATTTCCACACATTCGGTACGGCTACTCGATTGGATAGAGAAGACC

R  F  G  R  G  V  K  G  V  S  H  A  D  E  L  T  Y  L  F  W
```

FIG. 3D

```
      AACATTTTGTCGAAACGCCTGCCAAAGGAAAGCCGCGAATACAAAACCATTGAACGCATG
1441  ------+---------+---------+---------+---------+---------+ 1500
      TTGTAAAACAGCTTTGCGGACGGTTTCCTTTCGGCGCTTATGTTTTGGTAACTTGCGTAC

N  I  L  S  K  R  L  P  K  E  S  R  E  Y  K  T  I  E  R  M

GTTGGCATTTGGACGGAATTCGCCACCGGCCAAACCATACAGCAATGATATAGCCCGGC
1501  ------+---------+---------+---------+---------+---------+ 1560
      CAACCGTAAACCTGCCTTAAGCGGTGGCCGTTTGGTATGTCGTTACTATATCGGCCG

V  G  I  W  T  E  F  A  T  G  K  P  Y  S  N  D  I  A  G

ATGGAAAACCTCACCTGGGATCCCATAAAAAAATCCGATGATGTCTATAAATGTTTAAAT
1561  ------+---------+---------+---------+---------+---------+ 1620
      TACCTTTTGGAGTGGACCCTAGGGTATTTTTTTAGGCTACTACAGATATTTACAAATTTA

M  E  N  L  T  W  D  P  I  K  K  S  D  D  V  Y  K  C  L  N

ATCGGCGATGAATTGAAAGTTATGGATTTGCCAGAAATGGATAAAATTAAACAATGGGCA
1621  ------+---------+---------+---------+---------+---------+ 1680
      TAGCCGCTACTTAACTTTCAATACCTAAACGGTCTTTACCTATTTTAATTTGTTACCCGT

I  G  D  E  L  K  V  M  D  L  P  E  M  D  K  I  K  Q  W  A

AGTATATTCGATAAAAAGAAGGAATTGTTT
1681  ------+---------+---------+ 1710
      TCATATAAGCTATTTTTCTTCCTTAACAAA

S  I  F  D  K  K  K  E  L  F
```

FIG. 3E

```
SEQ ID NO:15 MdαE7   97  QTDEFISGKPTGSEDCLYLNVYTNDLNPDKKRPVMVFIHGGGFIFGEANRN  146
SEQ ID NO:43 LcαE7   97  QVDFITGKVCGSEDCLYLSVYTNNLNPETKRPVLVYIHGGGFIIGENHRD  146
                   147  WYGPDYFMKKPVVLVTVQYRLGVLGFLSLKSENLNVPGNAGLKDQVMALR  196
                   147  MYGPDYFIKKDVVLINIQYRLGALGFLSLNSEDLNVPGNAGLKDQVMALR  196
                   197  WFKSNIAIFGGDVDNITVFGESAGGASTHYMMITEQTRGLFHRGIMMSGN  246
                   197  WIKNNCANFGGNPDNITVFGESAGAASTHYMMLTEQTRGLFHRGILMSGN  246
                   247  SMCSSASTECQSRALTMAKRVGYKGEENEKDILEFLMKANPYDLIKEEPQ  296
                   247  AICPLANTQCQHRAFTLAKLAGYKGEDNDKDVLEFLMKAKPQDLIKLEEK  296
                   297  VLTPERM  303
                   297  VLTLEER  303
```

FIG. 4

MALATHION CARBOXYLESTERASE

This invention relates to an enzyme (and the nucleic acid sequences encoding this enzyme), termed malathion carboxylesterase (MCE) which is able to efficiently hydrolyse a specific class of organophosphate (OP) insecticides which have the general structures:

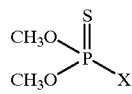

(eg. malathion, phenthoate)

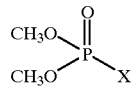

(eg. malaoxon, phenthoate oxon)
where X contains one or more carboxylester groups for thion type organophosphates but is unconstrained for oxon type organophosphates.

Residues of organophosphate insecticides are undesirable contaminants of the environment and a range of commodities. Areas of particular sensitivity include contamination of domestic water supplies and soil, residues above permissible levels in various food and fibre exports and contamination of domestic pets. Bioremediation strategies are therefore required for eliminating or reducing these insecticide residues. One proposed strategy involves the use of enzymes capable of immobilising or degrading the insecticide residues. Such enzymes may be employed, for example, in bioreactors through which contaminated water could be passed; in production animal dips to reduce problems with contaminated pasture and run off into water supplies; or in washing solutions after post harvest disinfestation of fruit, vegetables or animal products to reduce residue levels and withholding times. Suitable enzymes for degrading pesticide residues include esterases. It is desirable that the esterases be relatively specific and hydrolyse the pesticide residues at a rapid rate.

The MCE enzyme has been purified from different malathion resistant strains of *L. cuprina*, RM and der-L (Whyard S., Russell R. J. and Walker V. K., Biochemical Genetics 32: 9, 1994; Whyard S. and Walker V. K., Pesticide Biochemistry and Physiology 50: 198, 1994). It is a 60.5 kDa monomer with a $K_m$ for malathion of 11.0±0.4 μM and a $V_{max}$ of 775±28 nmol malathion/min/mg. It also has a high turnover rate for malathion ($k_{cat}$=46 min$^{-1}$).

In order to enable the production of useful amounts of the MCE enzyme the present inventors sought to clone the putative MCE gene from a malathion resistant strain of *L. cuprina*(RM-8) using PCR and cloning techniques.

The MCE gene in *L. cuprina* has been mapped using classical genetic techniques to a position within 0.7 map units from the E3 gene on chromosome 4. The likely homologue of MCE in *Drosophila melanogaster*, Mce, has been mapped to the right arm of chromosome 3 in the vicinity of the genes encoding the major α-carboxylesterase, EST 9, and the orthologue of *L. cuprina* E3, EST23 (Spackman M. E., Oakeshott J. G., Smyth K-A., Medveczky K. M., and Russell R. J., Biochemical Genetics, 32: 39, 1994).

In order to clone the MCE gene from *L. cuprina*, it was decided to use the wealth of molecular genetic techniques available for *D. melanogaster* to clone the MCE homologue and use these clones as probes to isolate the *L. cuprina* genes themselves.

In summary, five esterase amplicons were isolated from *L. cuprina* genomic and cDNA. Four of the five *L. cuprina* amplicons obtained by PCR using cluster specific primers were designated LcαE7, LcαE8, LcαE9 and LcαE10 on the basis of homology to the corresponding Drosophila genes. The fifth, Lc#53, could not be assigned with any confidence on the basis of similarity to any of the Drosophila genes.

MCE specific activity is highest in the adult head, rather than the thorax or abdomen (Smyth,K-M., Walker,V. K., Russell,R. J. and Oakeshott,J. G. Pesticide Biochemistry and Physiology, 54:48, 1996). On this basis, LcαE7, LcαE8 and LcαE10 were all MCE candidates. Previous physiological studies of Parker,A. P., Russell,R. J., Delves,A. C. and Oakeshott,J. G.(Pesticide Biochemistry and Physiology 41:305, 1991) have shown that the E3 (LcαE7) enzyme is present in the adult head. Moreover, the LcαE8 and LcαE0 genes are also expressed in the head since PCR using cluster-specific primers were able to amplify these genes from a head cDNA library. PCR failed to detect LcαE9 and Lc#53 in either larval fat body or adult head cDNA and Northern analysis of the *D. melanogaster* αE9 homologue indicated that this gene was only expressed in embryos. Therefore both LcαE9 and Lc#53 were discounted as candidates for the genes encoding E3 and MCE.

The LcαE8 and LcαE10 genes were initially chosen as prime MCE candidates on the basis of this distribution and due to the fact that it was known that LcαE7 encodes the E3 enzyme involved in diazinon/parathion OP resistance in *L. cuprina* (PCI/AU 95/00016: "Enzyme based bioremediation") and it was thought that malathion resistance and diazinon/parathion resistance were encode by separate genes.

The present inventors have made the surprising finding that it is a variant of LcαE7 which encodes the MCE enzyme. This gene has been expressed in vitro and the product shown to have MCE activity. The expressed product can be formulated for use in degrading environmental carboxylester or dimethyl general OPs.

Accordingly, in a first aspect, the present invention consists in an isolated DNA molecule encoding an enzyme capable of hydrolysing at least one organophosphate selected from the group consisting of carboxylester organophosphates and dimethyl-oxon organophosphates, the DNA molecule comprising a nucleotide sequence having at least 60%, preferably at least 80% and more preferably at least 95% homology with LcαE7, in which the protein encoded by the DNA molecule differs from E3 at least in the substitution of Trp at position 251 with an amino acid selected from the group consisting of Leu, Ser, Ala, Ile, Val, Thr, Cys, Met and Gly.

Figure 1D:
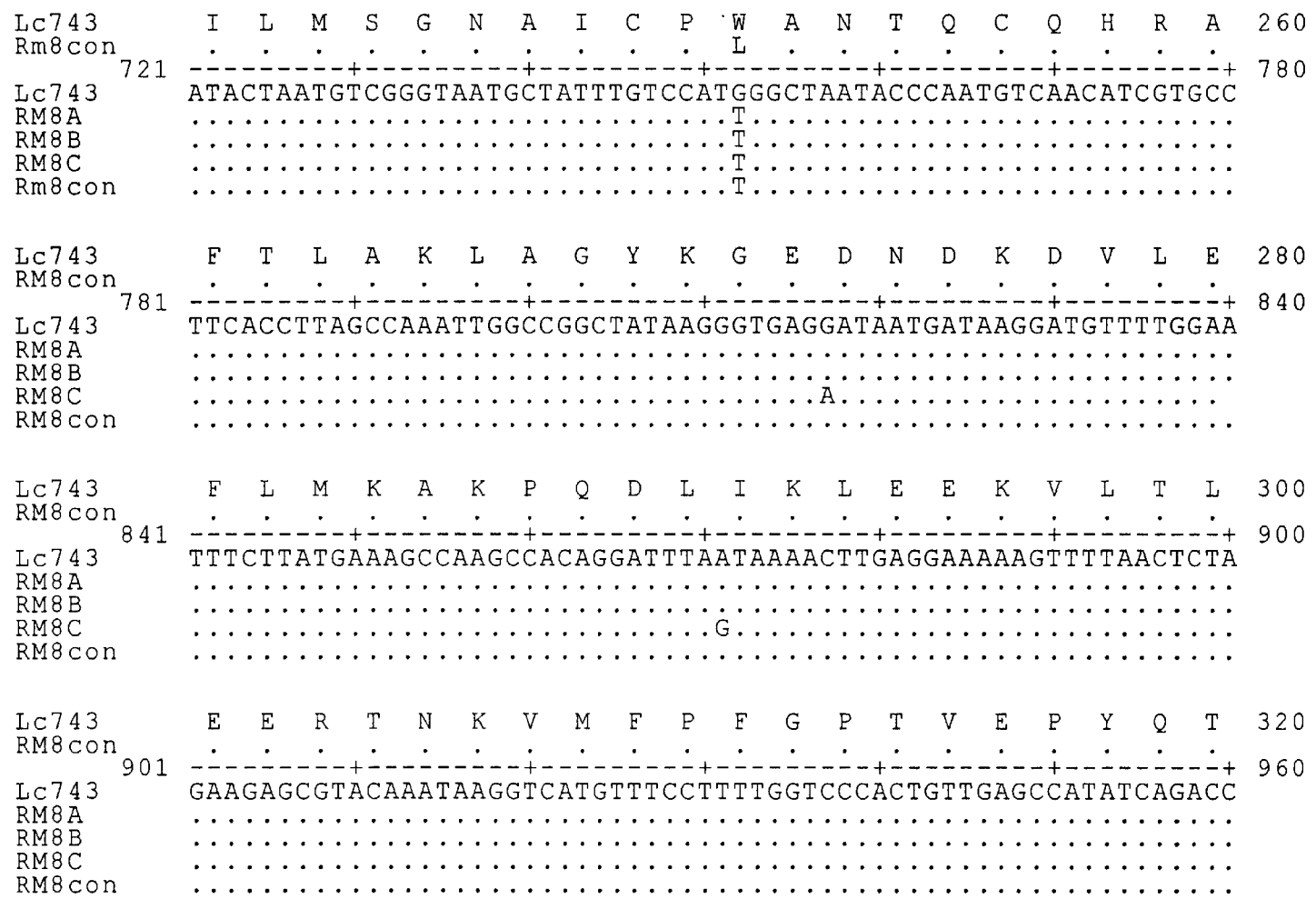
Figure 1E:
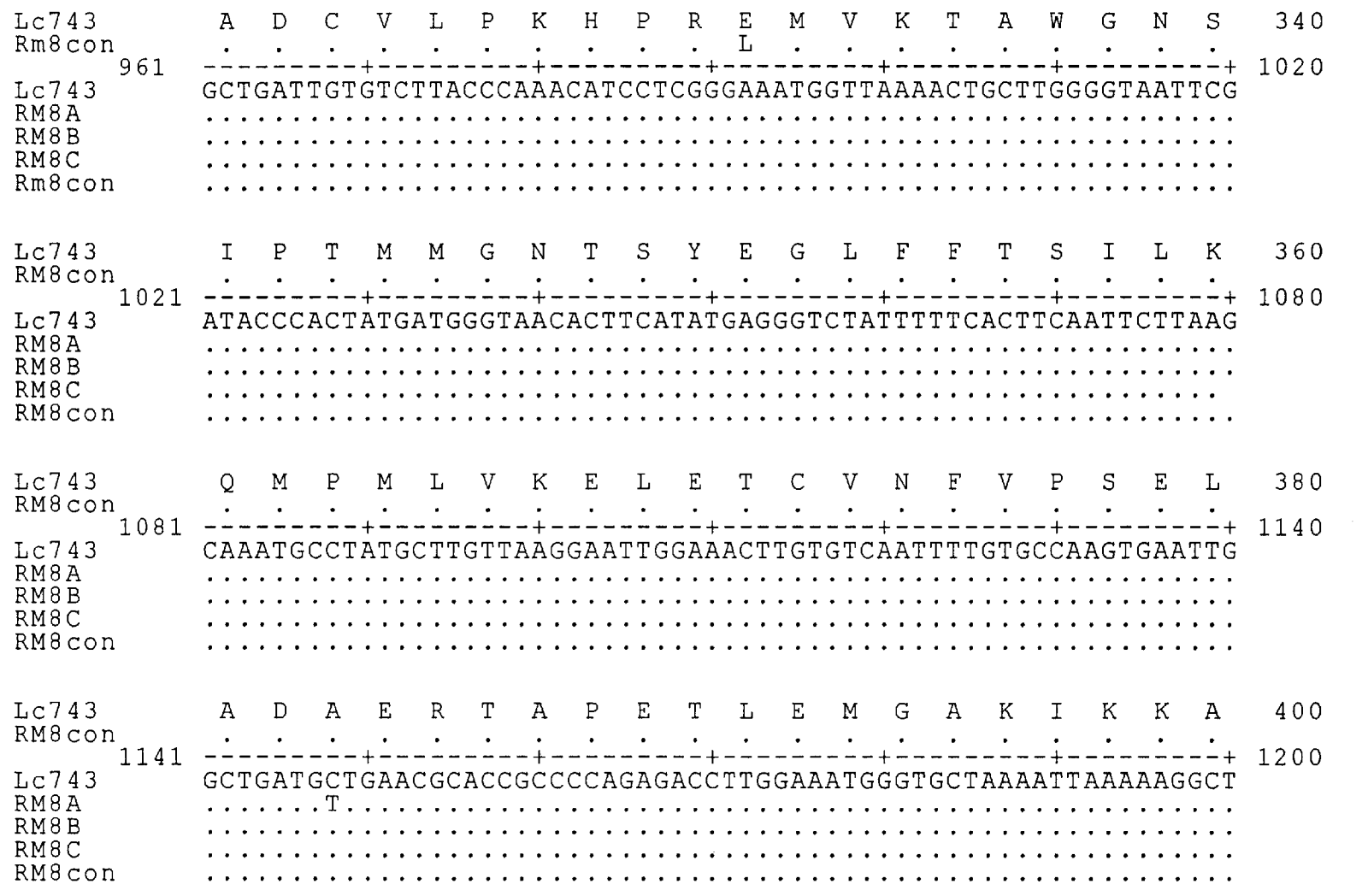

In a preferred embodiment the present invention the isolated DNA molecule has a sequence as shown in FIG. 1 or a sequence which hybridises thereto with the proviso that the protein encoded by the DNA molecule differs from E3 at least in the substitution of Trp at position 251 with an amino acid selected from the group consisting of Leu, Ser, Ala, Ile, Val, Thr, Cys, Met and Gly.

In a preferred embodiment of the present invention the Trp at position 251 is substituted with Ieu or Ser.

As is stated above the present invention includes nucleic acid molecules which hybridise to the sequence shown in FIG. 1. Preferably such hybridisation occurs at, or between, low and high stringency conditions. In general terms, low stringency conditions can be defined as 3xSCC at about ambient temperature to 65° C., and high stringency conditions as 0.1xSSC at about 65° C. SSC is the abbreviation of a buffer of 0.15M NaCl, 0.015M trisodium citrate. 3xSSC is three times as strong as SSC and so on.

In a second aspect the present invention consists in an isolated DNA molecule, the DNA molecule encoding a polypeptide having the amino acid sequence of RM-8 Con shown in FIG. 1 or the amino acid sequence of MdαE7 shown in FIG. 3 in which Trp at position 251 is replaced with Ser.

Homologues of the MCE encoding sequence may also be present in the genome of other insects, and particularly other species of Diptera. Thus, it is to be understood that the invention also extends to these homologues An example of this is provided by the results set out hereunder regarding Musca MCE.

The isolated DNA molecules of the present invention may be cloned into a suitable expression vector and subsequently transfected into a prokaryotic or eukaryotic host cell for expression of the enzyme. A particularly suitable system involves baculovirus vectors and an insect cell line.

In a third aspect the present invention consists in a method of producing an enzyme capable of hydrolysing at least one organophosphate selected from the group consisting of carboxylester organophosphates and dimethyl-oxon organophosphates, or an enzymatically active portion thereof, the method comprising transforming a host cell with the DNA molecule of the first aspect of the present invention operatively linked to a control sequence, culturing the transformed cell under conditions which allow expression of the DNA sequence and recovering the produced enzyme, or enzymatically active portion thereof.

It is also envisaged that as an alternative to using the enzyme per se as a bioremediation agent the bioremediation agent may be an organism transformed with the DNA encoding the enzyme. In such an arrangement the organism, transformed such that it expresses the enzyme, would be used as the bioremediation agent.

The invention further relates to methods for eliminating or reducing the concentration of carboxylester or dimethyl-oxon-type organophosphate insecticides residues in a contaminated sample or substance, involving the use of an esterase encoded by an isolated DNA molecule according to the present invention.

In order that the nature of the present invention may be more clearly understood preferred forms will now be described with reference to the following examples and Figures in which:

FIGS. 1A to 1H show multiple nucleotide alignment of the three malathion-resistant clones (RM8A–C) and their consensus (RM8con) with the reference susceptible clone (Lc743) of LcαE7 (E3). Dots indicate identity with the Lc743 susceptible clone. Below the ruler is the aligned nucleotide sequence and above is the inferred amino acid sequence of Lc743 with the one replacement found in Lc7RM8con indicated in bold text immediately below. Nucleotides are numbered from the predicted start of translation and amino acids from the predicted start methionine. Lc743 5' and Lc743 3' primer sequences are underlined.

FIGS. 2A and 2B show amino acid alignment of the inferred MdαE7 protein from the Rutgers strain of *Musca domestica* compared to the LcαE7 (E3) protein from the *Lucilia cuprina* Lc743 clone (PCT/AU95/00016 "Enzyme Based Bioremediation"). Sequence comparison shows a 75% identity and 86% similarity between the same length, 570 residue proteins. Arrow indicates the conserved tryptophan residue at position 251 of the alignment.

FIGS. 3A to 3E show the 1710 bp nucleotide coding sequence of the Rutgers strain MdαE7 gene. Also shown is the inferred 570 protein sequence.

FIG. 4 shows amino acid alignment of the PCR Ankara strain MdαE7 amplicon and the corresponding region of the RM-8 malathion resistant LcαE7 protein. The structural mutations conferring malathion resistance (serine for MdaE7 and Leucine for LcaE7) are indicated by arrow at residue position 251.

CLONING AND SEQUENCING OF THE MCE GENE FROM A MALATHION RESISTANT STRAIN OF *LUCILIA CUPRINA*

Two types of change in carboxylesterase activity have been associated with resistance to OP insecticides in the higher Diptera. One type of change results in resistance to OPs like diazinon and parathion, while the other results in resistance to OPs like malathion, with one or more carboxylester groups in addition to the phosphotriester moiety that defines it as an OP (see above).

The two types of change were first described among OP resistant strains of *Musca domestica*. In both types an increased degradation of OPs was associated with reduced ali-esterase activity, where "ali-esterase" refers to enzymes which are major contributors to the hydrolysis of the carboxylester, methyl butyrate, or similar molecules (Oppenoorth, F. J., Entomology Experimental and Applied, 2: 304, 1959; Oppenoorth F. J. and van Asperen, K., Entomology Experimental and Applied 4: 311, 1961). This led to the formulation of the "mutant ali-esterase hypothesis", which proposes that each type of resistance is due to a mutation in a specific carboxylesterase that simultaneously enables it to hydrolyse the phosphoester linkages common to the oxon form of all OPs and decreases its activity toward certain carboxylester substrates (Oppenoorth, F. J. and van Asperen, K., Science 132: 298, 1960).

Both types of change yielded resistance factors for diverse OPs (except malathion) in the range of about 2–30 fold (Bell, J. D. and Busvine, J. R., Entomology Experimental and Applied, 10: 263, 1967). However, the malathion resistant *M. domestica* strains also showed exceptionally high resistance to malathion (generally >100 fold). This high resistance was associated with cleavage of the carboxylester linkages in malathion (ie MCE activity) in addition to the hydrolysis of the phosphoester linkage (OP hydrolase activity). MCE activity accounted for the major breakdown products in vivo and in vitro (Townsend, M. G. and Busvine, J. R., Entomology Experimental and Applied 12: 243, 1969).

No recombination between the two types of resistance or between them and ali-esterase activity was observed among the *M. domestics* strains (Nguy, V. D. and Busvine, J. R., World Health Organisation 22: 531, 1960). This suggests that while they are clearly distinct in respect of OP hydrolase and MCE activities, the two types of resistance might nevertheless be allelic changes to the same carboxylesteraselali-esterase gene/enzyme system (Oppenoorth, F. J. and Welling,W., in Insecticide Biochemistry and Pharmacology, Wilkinson, C. F. ed., Plenum Press, New York and London, pp. 507–551, 1976).

A malathion resistance phenotype has also been described in the blowfly, *Chrysomya putoria*, which parallels the malathion resistance phenotype of *M. domestica* in that it is associated with high MCE and low ali-esterase activities (Busvine, J. R., Bell, J. D. and Guneidy, A. M., Bulletin of Entomological Research 54: 589, 1963; Bell, J. D. and Busvine, J. R., Entomology Experimental and Applied 10:

263, 1967; Townsend, M. G. and Busvine, J. R., Entomology Experimental and Applied 12: 243, 1969). Further evidence for the similarity of the malathion resistance phenotypes in the two species is indicated by the spectrum of OP compounds which synergise malathion. Specifically, among a series of symmetrical trisubstituted phosphorus compounds, the best synergists (eg triphenylphosphate) were common to both species (Bell, J. D. and Busvine, J. R., Entomology Experimental and Applied 10: 263, 1967). However, little is known of diazinon/parathion type resistance in C. putoria.

The mutant ali-esterase hypothesis has also been invoked to explain diazinon/parathion resistance in L. cuprina, because these flies hydrolyse paraoxon more rapidly than susceptible flies (Hughes, P. B. and Devonshire, A. L., Pesticide Biochemistry and Physiology 18:289, 1982) and resistance is associated with reduced carboxylesterase activity. In this case the esterase isozyme E3 from resistant flies is not detected ("non-staining") after polyacrylamide gel electrophoresis (PAGE; Hughes, P. B. and Raftos, D. A., Bulletin of Entomological Research 75: 535, 1985). Evidence for a causal connection between the E3 change and resistance was obtained by EMS mutagenesis of an E3 staining, OP susceptible strain of L. cuprina and selection for OP resistant mutants; all resistant mutants recovered had the E3 non-staining PAGE phenotype (McKenzie, J. A., Parker, A. G. and Yen, J. L., Genetics 130: 613, 1992).

Like malathion resistant strains of M. domestica, strains of L. cuprina that are resistant to malathion exhibit very high resistance factors towards malathion and enhanced MCE activity. Also in common with M. domestica, malathion resistant L. cuprina generally do not exhibit diazinon/parathion resistance, and vice versa. However, one difference from the situation in M. domestica is that the loci encoding the two resistance phenotypes appeared in some experiments to be genetically separable, albeit closely linked (Smyth, K-A., Russell, R. J. and Oakeshott, J. G., Biochemical Genetics 32: 437,1994; Smyth, K-A., Walker, V. K., Russell, R. J. and Oakeshott, J. G., Pesticide Biochemistry and Physiology 54: 48, 1996).

An esterase gene cluster containing genes involved in OP resistance has been isolated from L. cuprina (Newcomb, R. D., East, P. D., Russell, R. J. and Oakeshott, J. G., Insect Molecular Biology 5: 211, 1996). One of these genes, LcαE7, encodes esterase E3 (Newcomb, R. D., Campbell, P. M., Russell, R. J. and Oakeshott, J. G. Insect Biochemistry and Molecular Biology, in press), a structural mutation in the active site of which confers diazinon/parathion resistance on L. cuprina. These data are described in a previous patent application PCT/AU 95100016: "Enzyme based bioremediation", the disclosure of which is incorporated herein by reference.

Below we describe the cloning and sequencing of the LcαE7 gene from a malathion resistant strain of L. cuprina. We present molecular genetic evidence that this allele of esterase E3 is the MCE gene responsible for malathion resistance in L. cuprina.

a) Cloning the Malathion Resistant Allele of LcαE7

An RT-PCR (reverse transcriptase—PCR) approach was used to clone a cDNA allele of LcαE7 from a malathion resistant strain of L. cuprina (RM-8) which is homozygous for the fourth chromosome.

Adults from the RM-8 strain were aged for three days before collection and stored at −70° C. RNA was prepared using a modified protocol of Chigwin et al. (Chigwin, J. M., Przybyla, A. E., MacDonald, R. J. & Rutter, W. J., 1979, Biochemistry 18, 5294). About 100 adults were thoroughly homogenised in 15ml of solution D (4M guanidinium thiocyanate, 25 mM sodium citrate, pH 7.0, 0.5% sarkosyl, 0.1M β-mercaptoethanol) using a Sorvall Omnimix blender. The resulting homogenate was filtered through glasswool and 6 ml layered on top of 5 ml of 4.8M CsCl, made up in 10 mM Na- EDTA, pH 8, in an SW41 ultracentrifuge tube. These were spun at 35,000 rpm in an SW41 rotor for 16 hr at 15° C. The supernatant was removed and the RNA pellet resuspended in 400 µl of DEPC-treated H$_2$O. The RNA was precipitated by the addition of 800 µl of ethanol and 10 µl of 4M NaCl and stored under ethanol at −20° C. Before use the RNA pellet was washed in 75% ethanol and air dried before resuspension in DEPC-treated H$_2$O.

PolyA$^+$ RNA was prepared from 500 µg of total RNA using affinity chromatography on oligo-dT cellulose (Pharmacia; Sambrook, J., Fritsch, E. F., and Maniatis, T., 1989, Molecular Cloning: A Laboratory Manual, 2nd Edition, Cold Spring Harbor Laboratory Press, USA). The resulting mRNA (1–5 µg) was again precipitated, washed and resuspended in 20 µl of DEPC-treated H$_2$O. Oligo-dT primed cDNA was made from 1 µg of mRNA using reverse transcriptase (Superscript II, BRL) as per the manufacturers instructions in a 20 µl volume reaction. 200 ng of cDNA was used as template in each of two PCR reactions using primers designed from the 5' (Lc743 5':5' atgaatttcaacgttagtttgatggea 3') and complementary 3' (Lc743 3':5' ctaaaataaatctctat-gtttttcaaac 3') ends of the coding region of the LcαE7 gene. Reactions used Taq DNA polymerase (BRL) and contained 100 pmoles of each primer, 0.2 mM of each dNTP, 10 mM Tris-HCl, pH 8.3, 50 mM KCl, 0.002% Tween 20 (v/v), 1.5 mM MgCl$_2$, and 200 ng of template. Two drops of mineral oil were layered over each 50 µl reaction. Six units of Taq enzyme was added after a 5 minute "hot start" at 97° C. and was followed by 40 cycles of 35 seconds at 97° C., 1 minute at 60° C. and 2 minutes at 72° C. A final cycle of 72° C. for 8 minutes was included. The 1.7 kb major product was gel purified and cloned into the EcoRV cleavage site of the pBSK$^-$ (Stratagene) or pGEM-T (Promega) plasmid vectors using conventional cloning techniques (Sambrook, J., Fritsch, E. F., and Maniatis, T., 1989, Molecular Cloning: A Laboratory Manual, 2nd Edition, Cold Spring Harbor Laboratory Press, USA).

b) Sequencing the Malathion Resistant Allele of LcαE7

Methods:

Three clones were chosen for sequencing (RM8-A to -C ), all of which were derived from independent PCR reactions. A set of twelve 21-mer sequencing primers (sequence shown below) were designed from the listing LcαE7 sequence:

TABLE 1

| primer seq (5' - 3') | primer name | 5' position in Lc743 sequence (FIG. 1) |
|---|---|---|
| ggatggtgtgcgtgattgttg | 7F1 | 246 (SEQ ID NO:16) |
| aaaaggatgtggtgttgatta | 7F2 | 464 (SEQ ID NO:17) |
| actaatgtcgggtaatgctat | 7F3 | 723 (SEQ ID NO:18) |
| cactatgatgggtaacacttc | 7F4 | 1026 (SEQ ID NO:19) |
| tgttacaggagaaacaccaac | 7F5 | 1203 (SEQ ID NO:20) |
| agaatcgcgtgaatacaaaac | 7F6 | 1467 (SEQ ID NO:21) |
| acggtataccctcaaaactgt | 7R1 | 187 (SEQ ID NO:22) |
| tcccaaacgatattgtatgtt | 7R2 | 504 (SEQ ID NO:23) |
| acatcatgtagtgggtagaag | 7R3 | 685 (SEQ ID NO:24) |
| ccgaggatgtttgggtaagac | 7R4 | 990 (SEQ ID NO:25) |
| tatcagctgttggtgtttctc | 7R5 | 1231 (SEQ ID NO:26) |
| acgcgattctttaggcatacg | 7R6 | 1476 (SEQ ID NO:27) |

These were used in dye-terminator sequencing reactions (ABI) conducted following manufacturers instructions in 25 µl capillary tubes in a Corbett Research capillary thermal cycler, except that 50pmoles of primer was used per reaction, a "hot start" of 96° C. for 3 minutes was included and 30 cycles were completed for each sequencing reaction. Dye primer reactions were also conducted on all clones using the ABI M13 forward and reverse primers as per ABI protocols. Sequencing reactions were resolved by electrophoresis on an ABI 370A automatic sequencing machine as per the manufacturer's instructions. This resulted in both strands being sequenced entirely.

Results:

FIGS. 1A to 1H show a nucleotide and amino acid alignment of the three resistant clones (RM8 A–C) compared with the reference susceptible clone (Lc743) of LcαE7. A consensus sequence of the malathion-resistant LcαE7 allele was determined (RM-8con). Differences between resistant clones were assumed to be errors incorporated by the Taq polymerase.

Comparison of the susceptible sequence (Lc743) with that of the malathion-resistant RM-8 consensus sequence (RM-8con) identified only one replacement site difference, a Trp to Leu substitution at amino acid position 251 (nucleotide position 752). The homologous amino acid was highlighted on a three-dimensional model of *T. californica* AChE, revealing that the Leu mutation was situated at the base of the active site gorge, 6.5 Angstroms from the active site Ser.

c) Sequencing the Region Surrounding Nucleotide 752 from Various LcαE7 Alleles

An esterase structural mutation conferring malathion resistance would be expected to occur in the active site region of the molecule. The Trp to leu mutation at nucleotide position 752 in LcαE7 is therefore an excellent candidate for the malathion resistance mutation.

The inventors have established a total of 14 strains of *L. cuprina* which are homozygous for chromosome IV and of known malathion resistance status. These lines fall into seven classes on the basis of an RFLP analysis of genomic DNA using the LcαE7 gene as a probe. Nucleotide position 752 was therefore sampled over the entire range of classes.

Methods:

The complete cDNA sequence of the LcαE7 alleles from strains representing several of the classes are available. For example, the sequence of LcαE7 from RM-8 is shown in FIGS. 1A to 1H. Moreover, the LcαE7 cDNA sequences from strains LS2 and Llandillo 103, which represent two more classes, are described in patent application PCT/AU 95/00016 ("Enzyme based bioremediation"). The complete LcαE7 cDNA sequence of the Gunning 107 strain, representing a fourth class, is described in J. Trott, B.Agr.Sc Thesis, 1995.

To obtain the sequence of LcαE7 in the region of nucleotide 752 in strains LBB101, Landillo 104 and Hampton Hill 6.2, representing the remaining three classes, a PCR approach was taken. Genomic DNA was prepared from either eggs using the method of Davis, L. G., Dibner, M. D., and Batley, J. F., (1986. *Basis Methods in Molecular Biology*, Elsevier Science Publ. Co., New York, Section 5.3), or from adult flies using a C-TAB method (Crozier, Y. C., Koulianos, S. & Crozier, R. H., 1991, Experientia 47, 9668–969). 1 μg samples were then used as templates in PCR reactions using 100 pmoles of the primers 7F1 and 7R4. Also included in the reactions were 0.2 mM of each dNTP, 10 mM Tris-HCl, pH 8.3, 50 mM KCl, 1.5 mM MgCl₂. Two drops of mineral oil were layered over each 50 μl reaction. 2.5 units of Taq polymerase was added after a 'hot start' of 97° C. for 3 minutes while an annealing temperature of 55° was maintained. An initial extension at 72° C. was held for 2 minutes. This was followed by 34 rounds of 97° C. for 35 seconds, 55° C. for 1 minute and 72° C. for 1 minute. A final extension of 72° C. for 9 minutes was included. A single product of about 1 kb was produced. This was purified for sequencing using QIAquick spin columns (Qiagen), following manufacturers instructions. 500 ng of template was used in dye-terminator sequencing reactions using the 7F7 (5':5'tgctgcctctacccactacat 3') (SEQ ID NO: 28) and 7R7 (3':5' cctgtggcttggctttcataa 3' SEQ ID NO: 29) primers as described above.

Results:

Of the seven classes assayed, all five malathion-susceptible strains (LS2, LBB101, Llandillo 104, Gunning 107 and Llandillo 103) possess a G at nucleotide position 752, whereas both malathion-resistant strains (Hampton Hill 6.2 and RM-8) possess a T at this position, resulting in a Trp to Leu substitution at amino acid position 251 (Table 2). The presence of the same structural mutation in two malathion resistant strains with different fourth chromosomes strongly suggests that the mutation is responsible for resistance.

TABLE 2

| Strain | Malathion resistance status | Class | Residue at amino acid position 251[a] |
| --- | --- | --- | --- |
| LS2 | Susceptible | A | Trp |
| LBB101 | Susceptible | C | Trp |
| Llandillo 104 | Susceptible | B | Trp |
| RM-8 | Resistant | E | Leu |
| Hampton Hill 6.2 | Resistant | F | Leu |
| Llandillo 103 | Susceptible | D | Trp |
| Gunning 107 | Susceptible | G | Trp |

[a]Amino acid at position 251 corresponds to nucleotide position 752 in FIG. 1.

d) Cloning and Sequencing the Orthologous αE7 Gene from a Malathion Resistant Strain of *Musca domestica*

As described above, the diazinon/parathion and malathion esterase-mediated OP resistance types exhibit many striking parallels between *L. cuprina, M. domestica* and *C. putoria*, and are probably caused by functionally equivalent mutations in orthologous genes. The orthologous gene was therefore cloned from the housefly, *M. domestica*, and the region surrounding nucleotide 752 examined for the presence of the malathion resistance mutation in a malathion resistant Musca strain.

PCR Reactions;

Consensus generic a-esterase primers were designed to the conserved regions of the multiple amino acid alignments of *D. melanogaster* (Robin, C. Russell, R. J., Medveczky, K. M. and Oakeshott, R. J., Journal of Molecular Evolution 43: 241, 1996) and *L. cuprina* (Newcomb, R. D., Campbell, P. M., Russell, R. J. and Oakeshott, J. G. Insect Biochemistry and Molecular Biology, in press) α-esterase genes, and used in a PCR amplification experiment for the recovery of homologous αE7 gene sequence from *M. domestica*.

Genomic DNA was prepared using the Lifton method (Bender, W., Spierer, P. and Hogness, D. S., Journal of Molecular Biology 168: 17, 1989) from adult females of the Rutgers OP resistant housefly strain (Plapp, F. W. Jr., Tate, L. G. and Hodgson, E. 1976. Pestic. Biochem. Physiol. 6:175–182). Rutgers strain genomic DNA was used as the template in a 50 μl amplification reaction:

TABLE 3

| | Final concentration/amount |
|---|---|
| Template DNA | 100 ng |
| primer Md1 | 50 pmoles |
| primer Md2 | 50 pmoles |
| Buffer | 10 mM Tris-HCl (pH 8.3), 1.5 mM MgCl$_2$, 50 mM KCl |
| dNTP's | 0.25 mM (dATP, dCTP, dTTP, dGTP) |
| Taq polymerase | 1 unit |
| Total volume | 50 μl |

Primers:
Md1 (35 mer)
5' TTCGAGGGIATICCITAYGCIMARCCICCIBTNGG 3' (SEQ ID NO:30)
corresponding to residues 58–69 in *L. cuprina* αE7
Md2 (32 mer)
5' ACYTGRTCYTTIARICCIGCRTTICCIGGNAC 3' (SEQ ID NO:31)
corresponding to residues 92–82 in *L. cuprina* αE7
Note: IUB codes used for mixed positions; I = inosine.

PCR conditions over 38 cycles:

| 95° C. | 3' | | | | | | 1 cycle |
|---|---|---|---|---|---|---|---|
| 80° C. | | Hold (addition of 1 unit Taq polymerase) | | | | | |
| 95° C. | 1' | 50° C. | 1' | 72° C. | 1' | | 1 cycle |
| 95° C. | 1' | 55° C. | 1' | 72° C. | 1' | | 35 cycles |
| 95° C. | 1' | 55° C. | 1' | 72° C. | 4' | | 1 cycle |

Cloning and Sequencing PCR Amplicons:

The 540 bp major product was eluted from an agarose gel, purified using QIAGEN QIAquick PCR purification kit and cloned into the pGEM-T plasmid vector (PROMEGA) using standard techniques (Sambrook, J., Fritsch. E. F. and Maniatis, T., Molecular Cloning: A Laboratory Manual, Second Edition, Cold Spring Harbor Laboratory Press, USA, 1989). The ends of the cloned insert were sequenced using commercially available T7 and SP6 primers and TaqFS dye-terminator technology (ABI) on the Applied Biosystems Model 370A automated DNA sequencer. Translated amino acid sequences were aligned to predicted α-esterase protein sequences using PILEUP from the GCG computer package (Devereux, J., The GCG sequence analysis software package Version 6.0. Genetics Computer Group, University of Wisconsin Biotechnology Center, 1710 University Avenue, Madison, Wis., USA, 1989); all proved to be homologous to the sequences of known α-esterase genes from *D. melanogaster* and *L. cuprina*. The cloned 534 bp amplicon showed 76% identity over the equivalent 135 amino acids of the *L. cuprina* αE7 predicted protein sequence.

Isolation of the Complete αE7 Gene from *M. Domestica*:

A λDASH (Stratagene) genomic library of the Rutgers strain of *M. domestica* (Koener, J. F., Carino, F. A. and Feyereisen, R., Insect Biochemistry and Molecular Biology 23:439, 1993) was screened for a full-length genomic clone of αE7. Approximately 300,000 plaques were probed with the $^{32}$P labelled 534 bp amplicon described above. Library screening using conventional techniques (Sambrook, J., Fritsch. E. F. and Maniatis, T., Molecular Cloning: A Laboratory Manual, Second Edition, Cold Spring Harbor Laboratory Press, USA, 1989) was performed at high stringency (50% formamide, 5X SSC, 3X Denhardt's, 0.5% SDS and 10 μg/ml salmon sperm DNA at 45° C.) and included a final high stringency wash (0.1% SSC, 0.1% SDS at 65° C.). Restriction mapping indicated that a single λDASH clone with a 17.5 kb genomic insert contained the αE7 gene. A 4.5 kb HindIII fragment was subcloned into the pBSK vector (Stratagene) and characterised using dye-terminator automatic sequencing technology, as described above. A set a thirteen sequencing primers were designed and used to interpret the full length genomic sequence:

TABLE 4

| primer name | 5' - 3' primer sequence | size | 5' position in MdαE7 coding sequence (FIG. 3) |
|---|---|---|---|
| T7 | end sequencing of 4.5 kb pBSK⁻ clone | | polycloning site |
| T3 | end sequencing of 4.5 kb pBSK⁻ clone | | polycloning site |
| AE7.1 | TTTGGTCCCGACTACTTTATGA | 22 mer | 442 (SEQ ID NO:32) |
| AE7.2 | TGCCACTTATGAAATCTGTCTGTA | 24 mer | 310 (SEQ ID NO:33) |
| AE7.3 | TACATGATGATAACCGAACAGACC | 24 mer | 676 (SEQ ID NO:34) |
| AE7.4 | TCGATTATTTGGGTTTCATTTGT | 23 mer | 107 (SEQ ID NO:35) |
| AE7.5 | ACAGACAGATTTCATAAGTGG | 21 mer | 288 (SEQ ID NO:36) |
| AE7.6 | TTTGCATTCTTTCGGGTGTCA | 21 mer | 913 (SEQ ID NO:37) |
| AE7.7 | ATTCGATACCCACATTGATAG | 21 mer | 1016 (SEQ ID NO:38) |
| AE7.8 | GGCACTCCCATTTATTTGTAT | 21 mer | 1312 (SEQ ID NO:39) |
| AE7.10 | ATGACTTTTCTGAAGCAATTCAT | 23 mer | 1 (SEQ ID NO:40) |
| AE7.11 | AAACAATTCCTTCTTTTTATCGA | 23 mer | 1710 (SEQ ID NO:41) |
| AE7.12 | GGCATGGAAAACCTCACCTGG | 21 mer | 1558 (SEQ ID NO:42) |

The predicted coding sequence of 1710 bp or 570 amino acids showed a very high 75% identity and 85% similarity to the equivalent full length 570 residues of the αE7 protein from *L. cuprina* (FIGS. 2 and 3). Southern hybridisation analysis as per standard methods (Sambrook, J., Fritsch. E. F. and Maniatis, T., Molecular Cloning: A Laboratory Manual, Second Edition, Cold Spring Harbor Laboratory Press, USA, 1989) of a probe and EcoRI, Hind III, Sal I digested DNA, showed a single 4.5 kb hybridising band for the HindIII digest, a single 6.0 kb SaiII band and two EcoRI bands of 1.5 kb and 0.8 kb. The analysis confirms the restriction pattern interpreted from the sequencing and mapping data of the lambda genomic clone. No other aberrant hybridisation patterns occurred indicating a high probability that αE7 exists as a single copy gene.

Characterisation of a Putative αE7 Malathion Resistant Allele of *M. domestic*:

Genomic DNA extracted (Bender, W., Spierer, P. and Hogness, D. S., Journal of Molecular Biology 168: 17, 1989)

from single adult female flies of the highly malathion resistant Ankara strain (Sisli, M. N., Bosgelmez, A., Kocak, O., and Porsuk, H. 1983. Mikrobiyol Bul. 17:49–46) was used for sequence characterisation of a putative malathion resistance allele. A series of PCR reactions were performed using single fly genomic DNA for the characterisation of allelic variants of the αE7 gene. PCR amplification using conditions described above, with the specific housefly AE7.5 and AE7.6 primer pair, produced single amplicons of approximately 760 bp. This amplicon encompasses the highly conserved region involved in the catalytic site of the enzyme, coding for residues 96–304 of the translated sequence, including the site of the Trp to Leu mutation at amino acid residue 251 associated with malathion resistance in L. cuprina (FIG. 4). Cloning and sequencing of PCR amplicons (described earlier) from nine individual flies showed that the Ankara strain segregates for two allelic variants of the αE7 gene: one has a Trp residue at amino acid position 251, whereas the other has a Ser at this same position. This replacement is synonymous with the Trp to Leu substitution involved in malathion resistance in L. cuprina. Both leucine and serine replace a bulky tryptophan residue within the active site and we therefore propose that this change accounts for the observed changes in the kinetic properties of the enzymes towards carboxylesters and OPs. In a similar manner it is believed that the substitution of the bulky Trp residue with other smaller residues such as Ala, Ile, Gly, Val, Thr, Cys and Met will have a similar effect. The finding of these similar active site mutations in malathion resistant strains of both Lucilia and Musca further supports our conclusion that these mutations are responsible for malathion resistance in these species.

Hydrolytic Activity of the Expressed Products of the Susceptible and Malathion Resistant Alleles of LcαE7

Below we describe the activities of the expressed products of the susceptible and malathion resistant alleles of LcαE7 for various carboxylester and OP substrates. The results suggest a possible mechanism for malathion resistance in L. cuprina as a result of the mutation at nucleotide 752 in the LcαE7 gene a) In vitro Expression The in vitro expression of the OP susceptible allele of LcαE7 (clone Lc743) is described in patent application PCT/AU 95/00016 ("Enzyme based bioremediation").

The malathion resistant LcαE7 full-length cDNA was cloned into the baculovirus transfer vector, Bacpac 6 (Clonetech) 3' of the polyhedrin promoter. Transfections were conducted using a lipofection method with DOTAP (Boehringer Mannheim) as per King and Possee (The Baculovirus Expression System: A Laboratory Guide, Chapman & Hall, London, 1992). One µg of DNA of each of the resulting constructs together with 200 ng of Bacpac 6 baculovirus DNA (Clonetech), linearised by digestion with the restriction enzyme BSU 361 (Promega), was incubated in a solution of HBS (hepes buffered saline) containing 15% DOTAP (Boehringer Mannheim) in a polystyrene container at room temperature for 10 minutes. The solution was then used to transfect a single well of a six well tissue culture plate pre-seeded 2 hrs previously with $10^4$ Sf9 (Spodoptera frugiperda) cells in 1.5 mls Grace's medium (King and Possee, The Baculovirus Expression System: A Laboratory Guide, Chapman & Hall, London, 1992). After 12 hours, the medium was replaced with 3 mls of Grace's medium containing 10% fetal calf serum. Construct plus DOTAP, linearised virus plus DOTAP and DOTAP only controls were conducted in parallel with transfections. The transfections were harvested 4–5 days after infection and the cells isolated by centrifugation at 500 g for 5 minutes. Aliquots of the resulting cell pellets were immediately stored on ice, resuspended in 10 mM imidazole-HCl buffer, pH 7.0, containing 0.5% Triton X-100. Final protein concentrations in these cell extracts were between 5 and 40 mg/ml. Aliquots of the cell extracts were stored at −70° C. prior to enzyme assays.

b) Malathion Hydrolysis

Methods:

MCE activity was assayed using the partition method of Ziegler, R., Whyard, S., Downe, A. E. R., Wyatt, G. R. and Walker, V. K., Pesticide Biochemistry and Physiology, 28:279 (1987) as modified by Whyard, S., Russell, R. J. and Walker V. K. Biochemical Genetics 32:9 (1994). Cell extracts were diluted 300-fold in 10 mM imidazole-HCl, pH 7.0, and 150 µl aliquots were placed in triplicate microfuge tubes. Reactions were started by the addition of 1 µl ethanol containing [$^{14}$C]-malathion [Amersham; 103 mCi/mmole, 280 nCi, labelled at both the methylene carbons of the succinate moiety, adjusted to 15 mM (or 375µM–15 mM for kinetic experiments) by the addition of unlabelled malathion (99%; Riedel-de-Haën Ag., Seelze, Germany)]. The assay mixture was incubated at 25° C. for 10 minutes, then 300 µl of dilution buffer was added and the undegraded malathion extracted three times with 600 µl of chloroform. The concentration of carboxylic acids of malathion in 300 µl of aqueous phase was determined by liquid scintillation. Protein concentrations in the cell supernatants were determined using the Biorad Protein Assay Kit by the method of Bradford, M., Analytical Biochemistry 72:248 (1976) with bovine serum albumin as the standard. Boiled enzyme controls were performed routinely. The specific MCE activity of an extract of cells infected with non-recombinant baculovirus was at least 700-fold lower than that of cells infected with baculovirus encoding OP-susceptible or malathion-resistance alleles of LcαE7. This slight MCE activity that was not due to alleles of LcαE7 was deemed a very minor source or error and subsequently ignored.

Results:

Using initial concentrations of malathion between 2.5 and 100 µM, MCE encoded by malathion resistant and susceptible alleles of LcαE7 exhibited a good fit to Michaelis-Menten kinetics. $K_m$ and $V_{max}$ were calculated for both enzymes. $K_{cat}$ was then calculated from the $V_{max}$ and the molarity of the LcαE7 products in their respective cell extracts. The molarity of susceptible LcαE7 product in the cell extract was determined by titration with paraoxon as previously described in Newcomb, R. D., Campbell, P. M., Russell, R. J. and Oakeshott, J. G., Insect Biochemistry and Molecular Biology (in press). The molarity of the product of the malathion resistant allele of LcαE7 was determined similarly, except that triphenylphosphate (TPP; 1 to $10 \times 10^{-8}$M) was used instead of paraoxon. In a control experiment TPP ($8 \times 10^{-8}$M) was preincubated with cell extract in triplicate for 15, 30 or 45 minutes prior to addition of the substrate malathion. There was no significant difference between the residual MCE activity at each of the preincubation times, indicating firstly that the inhibition of MCE by TPP had gone to completion and secondly, that TPP was not being turned over by MCE.

The kinetic parameters for malathion hydrolysis for the products of the malathion resistant and susceptible alleles of LcαE7 are:

TABLE 5

| Expressed LcαE7 Gene Product | $K_m$ (μM) | $K_{cat}$ (min$^{-1}$) |
| --- | --- | --- |
| Malathion susceptible (strain LS2) | 200 ± 30 | 70 ± 11 |
| Malathion resistant (strain RM-8) | 21 ± 1 | 43 ± 1 |

The $K_m$ and $K_{cat}$ for the malathion resistant product are in reasonable agreement with those determined for the MCE enzyme purified from malathion resistant flies (11±0.4 μM and 46±2 per min, respectively; Whyard, S. and Walker, V. K., Pesticide Biochemistry and Physiology, 50: 198, 1994).

c) Sensitivity of MCE Activity to TPP

High sensitivity to inhibition by TPP is a distinctive characteristic of the MCE activity associated with malathion resistance in M. domestica, C. putoria and L. cuprina, consistent with potent synergism of malathion by TPP in resistant strains of these species (Shono, T., Applied and Entomological Zoology 18: 407, 1983; Bell, J. D. and Busvine, J. R., Entomology Experimental and Applied 10: 263, 1967; Townsend, M. G. and Busvine, J. R., Entomology Experimental and Applied 12: 243, 1969; Hughes, P. B., Green, P. E. and Reichmann, K. G., Journal of Economic Entomology 77: 1400, 1984; Smyth, K-A., Walker, V. K., Russell, R. J. and Oakeshott, J. G., Pesticide Biochemistry and Physiology, 54: 48, 1996). MCE activity encoded by the malathion resistant allele of LcαE7 is potently inhibited by TPP, as indicated by stoichiometric inhibition of the enzyme at concentrations below $10^{-7}$M (see above).

d) α-Naphthyl Acetate Hydrolysis

Methods:

The initial rates of reactions between cell extracts containing the expressed products of the malathion resistant and susceptible LcαE7 alleles and a-naphthyl acetate (α-NA) were determined at 25° C. using a recording spectrophotometer and the method of Mastrapaolo and Yourno (Analytical Biochemistry 115: 188, 1981). 6–200 μM α-NA dissolved in 10 μl of 2-methoxyethanol was added to 0.1 M Tris-HCl pH 8.0 (980 μl) in a quartz cuvette. α-Naphthyl acetate is slowly hydrolysed in water so a background rate was recorded before starting the enzymic reaction by the addition of 10 μl of diluted cell extract. Control reactions were performed with extracts of both uninfected cells and Bacpac 6 infected cells. These controls exhibited negligible enzymic hydrolysis.

Results:

Using initial concentrations of α-NA from 6 to 200 μM, the enzymes encoded by the malathion resistant and susceptible alleles of LcαE7 exhibited a good fit to Michaelis-Menten kinetics. $K_m$ and $V_{max}$ were calculated for both enzymes. $K_{cat}$ was then calculated from the $V_{max}$ and the molarity of the LcαE7 products in their respective cell extracts (determined above).

TABLE 6

| Expressed LcαE7 Gene Product | $K_m$ (μM) | $K_{cat}$ (min$^{-1}$) |
| --- | --- | --- |
| Malathion susceptible (strain LS2) | 70 ± 5 | 11,000 ± 300 |
| Malathion resistant (strain RM-8) | 150 ± 50 | 2270 ± 30 |

The $K_m$ and $K_{cat}$ for the malathion resistant product are in reasonable agreement with those determined for the MCE enzyme purified from malathion resistant flies (167±14 μM and 2063 per min; Whyard, S. and Walker, V. K., Pesticide Biochemistry and Physiology, 50: 198, 1994).

e) α-Napthyl Butyrate Hydrolysis

Methods:

As described above for α-NA hydrolysis except that 6–200 μM α-naphthyl butyrate (α-NB) was used instead of α-NA.

Results:

Using initial concentrations of α-NB from 6 to 200 μM, the enzymes encoded by the malathion resistant and susceptible alleles of LcαE7 exhibited a good fit to Michaelis-Menten kinetics. $K_m$ and $V_{max}$ were calculated for both enzymes. $K_{cat}$ was then calculated from the $V_{max}$ and the molarity of the LcαE7 products in their respective cell extracts (determined above).

TABLE 7

| Expressed LcαE7 Gene Product | $K_m$ (μM) | $K_{cat}$ (min$^{-1}$) |
| --- | --- | --- |
| Malathion susceptible (strain LS2) | 20 ± 5 | 18,000 ± 2,000 |
| Malathion resistant (strain RM-8) | 29 ± 4 | 9,000 ± 400 |

The $K_m$ and $K_{cat}$ for the malathion resistant product are in reasonable agreement with those determined for the MCE enzyme purified from malathion resistant flies (39±4 μM and 3700 per min; Whyard, S. and Walker, V. K., Pesticide Biochemistry and Physiology, 50: 198, 1994).

f) General OP Hydrolysis

In M. domestics there is a pattern of cross-resistance among OPs (Bell, J. D. and Busvine, J. R., Entomology Experimental and Applied 10: 263, 1967) such that parathion/diazinon resistant flies generally exhibit greater resistance factors towards OPs with two ethoxy groups attached to the phosphorus atom ('diethyl OPs') rather than two methoxy groups ('dimethyl OPs'). The converse pattern (ie greater resistance to dimethyl OPs) was observed for malathion resistant strains of M. domestica and C. putoria (Bell, J. D. and Busvine, J. R., Entomology Experimental and Applied 10: 263, 1967; Townsend, M. G. and Busvine, J. R., Entomology Experimental and Applied 12: 243, 1969). This dimethyl OP preference applies both to malathion analogues (with carboxylester groups) and general OPs (without carboxylester groups). The implication of these studies is that there is a general OP hydrolase activity intimately associated with malathion type resistance and that this OP hydrolase exhibits a preference for dimethyl OPs.

There are insufficient published data to determine whether such a dimethyl/diethyl OP cross-resistance pattern occurs in L. cuprina. Here we determine firstly that there is such a cross resistance pattern and secondly that the enzyme encoded by the malathion resistance allele of LcαE7 has hydrolytic activity against OPs which lack carboxylester groups.

Methods:

i) Toxicology:

The following organophosphorus compounds were used: diazinon (O,O-diethyl O-2-isopropyl-6-methylpyrimidin-4-yl phosphorothioate, 91%, Mallinckrodt), parathion-methyl (O,O-dimethyl O-4-nitrophenyl phosphorothioate, 97.0%, Bayer), parathion (O,Odiethyl O-4-nitrophenyl phosphorothioate, 99%, Pestanal grade, Riedel-de-Haen), fenthion (O,O-dimethyl O-[3-methyl-4-(methylthio)phenyl] phosphorothioate, 98.8%, Bayer), fenthionethyl (O,O-diethyl O-[3-methyl-4-(methylthio)phenyl] phosphorothioate, a gift from Dr. G. Levot), dichlorvos (2,2-dichlorovinyl dimethyl phosphate, 99%, Chem Service), diethyl-dichlorvos (2,2-dichlorovinyl diethyl phosphate, a gift from Dr. J. Desmarchelier), di-isopropyl-dichlorvos (2,2dichlorovinyl di-isopropyl phosphate, a gift from Dr. J. Desmarchelier), malathion (S-1,2-bis (ethoxycarbonyl)ethyl O,O-dimethyl phosphorodithioate, technical grade, Nufarm), isopropyl malathion (S-1,2-bis (ethoxycarbonyl)ethyl O,O-di-isopropyl phosphorodithioate, a gift from Dr. J. Desmarchelier).

The toxicity of OPs in adult female *L. cuprina* was determined 3 or 4 days post-eclosion by application of OPs to the scutellum in 0.7 $\mu$l dioctylphthalate (Busvine, J. R., Bell, J. D. and Guneidy, A. M., Bulletin of Entomological Research 54: 589, 1963;; Townsend, M. G. and Busvine, J. R., Entomology Experimental and Applied 12: 243, 1969). Each OP was applied to at least 20 flies at each of at least 5 different concentrations, spanning the dose causing 50% mortality ($LD_{50}$). Control groups were treated with solvent but no OP. Mortality was determined 24 hours later. Data were fitted to the probit curve using the Probit Or LOgit (POLO-PC) computer program (LeOra Software, 1987). This program corrects for natural mortality which was <5%. The statistic g ("index of significance for potency estimation") was always less than 0.5 for the 95% confidence limits of $LD_{50}$.

ii) Chlorfenvinphos Hydrolysis Assay:

Enzyme samples were diluted in 0.1 M imidazole-HCl buffer pH 7.0 ("imidazole buffer") to a final volume of 50$\mu$l. Reactions were started by the addition 0.5 $\mu$l of ($^{14}$C-ethyl)-chlorfenvinphos (CVP, 306.5 MBq/mmole, Internationale Isotope Munchen) from a 7.5 mM stock solution in ethanol. The reaction was incubated at 30° C. and stopped by the addition of 300 $\mu$l dichloromethane and 150 $\mu$l of water followed by vigorous vortex mixing. The reactions were centrifuged to separate phases and 150 $\mu$l of the upper, aqueous phase was taken for scintillation counting to determine the amount of $^{14}$C-diethylphosphate produced by hydrolysis of CVP. Incubations with boiled enzyme were also performed to control for non-enzyme hydrolysis of CVP.

Results:

I) Toxicology:

$LD_{50}$s of 10 OPs were determined for the Woodside 5.2 strain (homozygous for a malathion resistance allele of Lc$\alpha$E7) and the Llandillo 103 strain (homozygous for a parathion/diazinon resistance allele of Lc$\alpha$E7). $LD_{50}$s were also determined for the OP susceptible LS2 strain in order to calculate resistance factors (Table 8). Woodside 5.2 flies exhibited about two- to five-fold greater resistance factors towards the dimethyl OPs, parathion-methyl, fenthion and dichlorvos than to their diethyl analogues, parathion, fenthion-ethyl and ethyl dichlorvos. Conversely, Llandillo 103 flies exhibited about two-fold greater resistance factors towards the diethyl OPs, parathion and ethyl dichlorvos, than to their dimethyl analogues, parathion-methyl and dichlorvos. However, there was no significant difference between the resistance factors of Llandillo 103 flies for fenthion and fenthion-ethyl.

Among four diethyl OPs, Llandillo 103 flies have higher resistance factors than Woodside 5.2 flies (except fenthion-ethyl with similar resistance factors; Table 8). In contrast, Woodside 5.2 flies have higher resistance factors than Llandillo 103 for each of four dimethyl OPs. Thus both strains exhibit general OP resistance of similar potency, albeit with a bias towards either dimethyl or diethyl OPs.

Neither resistant strain exhibited more than 3-fold resistance to the di-isopropyl analogues of dichlorvos or malathion (Table 8).

Comparable data from *M. domestics* are available for seven of the test compounds. In each case resistance factors are similar in strains of the two species exhibiting parallel resistance types (Table 8).

TABLE 8

OP cross-resistance patterns in adult *L. cuprina* with comparisons to *M. domestica*

| OP Compounds[1] | $LD_{50}{}^2$ LS2 (OP Susceptible) | $LD_{50}$ Llandillo 103 (Dz/para Resistant) | $LD_{50}$ Woodside 5.2 (Mal Resistant) | RF[3] (Dz/para R) | RF (Mal R) |
|---|---|---|---|---|---|
| Diazinon (E) | 57 (40–79), 3.5 ± 0.5 | 550 (490–630), 4.9 ± 0.7 | 270 (240–300), 5.1 ± 0.6 | 10 (20) | 5 (2) |
| Parathion-methyl (M) | 16 (11–20), 6.5 ± 0.8 | 185 (141–244), 3.4 ± 0.5 | 430 (390–490), 9.7 ± 1.5 | 12 (9) | 27 (10) |
| Parathion (E) | 52 (48–55), 9.2 ± 1.1 | 1050 (890–1280), 6.8 ± 1.2 | 290 (270–310), 13.3 ± 2.3 | 20 (35) | 6 (3) |
| Fenthion (M) | 61 (42–87), 5.2 ± 0.7 | 210 (180–240) 8.7 ± 1.5 | 320 (210–490) 3.9 ± 0.7 | 3 (3) | 5 (7) |
| Fenthion-ethyl (E) | 330 (290–370) 7.4 ± 1.1 | 690 (570–830) 8.7 ± 1.5 | 730 (660–870) 13.4 ± 2.6 | 2 | 2 |
| Dichlorvos (M) | 41 (35–51), 8.2 ± 1.1 | 150 (95–190), 5.1 ± 0.8 | 270 (210–340), 6.3 ± 1.0 | 4 (3) | 7 (6) |
| Ethyl Dichlorvos (E) | 360 (300–420), 5.0 ± 0.8 | 2370 (2320–2410), 54 ± 14 | 1100 (700–1500) 4.9 ± 1.2 | 7 | 3 |
| Isopropyl Dichlorvos (P) | 3500 (2200–4800), 4.1 ± 0.6 | 4600 (3400–5900) 4.1 ± 0.5 | 10200 (8800–12000) 8.1 ± 1.4 | NS | 3 |
| Malathion (M) | 550 (480–610), 6.4 ± 1.2 | 490 (360–600) 4.2 ± 0.9 | 4 | NS (2) | >130 (157) |
| Isopropyl Malathion (P) | 3600 (2700–4900), 6.3 ± 0.7 | 4900 (3700–6200), 8.5 ± 1.7 | 6400 (5900–7100), 10.1 ± 1.8 | NS | 1.8 (4) |

[1]Dimethyl (M), diethyl (E) or di-isopropyl (P) OPs.
[2]$LD_{50}$ (ng/fly) with 95% confidence limits, slope and standard error of the probit regression line.
[3]Resistance Factors: ratio of the $LD_{50}$ of Llandillo 103 or Woodside 5.2 with the $LD_{50}$ of LS2. "NS" indicates an RF not significantly different from unity. Resistance factors of *M. domestica* of the appropriate resistance type are shown in parentheses (Bell, J. D. and Busvine, J. R., Entomology Experimental and Applied 10: 263, 1967; ; Townsend, M. G. and Busvine, J. R., Entomology Experimental and Applied 12: 243, 1969).
[4]No mortality at this dose.

ii) Chlorfenvinphos Hydrolytic Activity of Whole Fly Homogenates and Expressed LcαE7 Gene Products:

Whole fly homogenates of malathion resistant (strains RM-8, 60NE 1.1, 4.2, Beverly 6.2, Hampton Hill 6.1, Hampton Hill 6.2, Woodside 5.2, Rop Rmal 1, M22.2 6.3, M27.1 4.1), diazinon resistant (Gunning 107, Inverell 22, Q4, RM2.6, Llandillo 103, Sunbury 5.2) and susceptible (LBB 101, Llandillo 104, LS2) strains of *L. cuprina* were tested for esterase-mediated hydrolysis of CVP, a general OP (ie not a malathion-type OP). All 10 malathion resistant strains had greater CVP hydrolytic activities (1.5–3.0 pmol/min/mg) than the 3 susceptible strains (0.5–1.0 pmol/min/mg, but less activity than the 6 diazinon resistant strains (8.2–30.0 pmol/min/mg).

The expressed product of the malathion resistant LcαE7 allele was tested for CVP hydrolytic activity. Turnover of 75 $\mu$M CVP was about 1.2 hour$^{-1}$, which is approximately 50-fold less than that of the diazinon resistant (RM2-6) LcαE7 gene product but much greater than that of the OP-susceptible (LS2) gene product, for which CVP activity was undetectable. [The CVP hydrolytic activity of the gene products of the RM2-6 and LS2 alleles of LcαE7 are described in patent application PCT/AU 95/00016: "Enzyme based bioremediation"].

g) Conclusions

1. We have discovered that dimethyl versus diethyl patterns of OP cross-resistance among strains of *L. cuprina* parallel those of OP resistant strains of *M. domestica* and *C. putoria*. The two OP resistance types are equally potent and general among most OPs (excluding malathion), albeit with a dimethyl or diethyl OP preference.

2. Diethyl OP hydrolytic activities encoded by the OP susceptible allele (nil), the malathion resistant allele (1.2 hour$^{-1}$) and the diazinon/parathion resistant alleles of LcαE7 (~1 min$^{-1}$) parallel the diethyl OP hydrolytic activities in homogenates of OP susceptible (low), malathion resistant (intermediate) and diazinon/parathion resistant (high) *L. cuprina* strains.

3. Taking points 1 and 2 together we propose that the dimethyl versus diethyl pattern of general OP cross resistance reflects the substrate specificity of the general OP hydrolase activities encoded by the two alternative OP resistance alleles of the αE7 gene. Thus we expect that products of malathion resistance alleles of αE7 genes from *L. cuprina* and *M. domestica* will exhibit dimethyl OP hydrolysis with kinetics that are as favourable for bioremediation as the diazinon/parathion resistance αE7 alleles are for diethyl OPs.

4. The enhanced MCE activity of the product of the malathion resistance alleles of αE7 genes causes flies to survive more than 100-fold greater doses of malathion. The MCE activity is enhanced in two ways. Firstly, it has more favourable kinetics for malathion breakdown than that of the susceptible allele ($K_{cat}/K_m$ is 6-fold greater). Secondly, it has acquired general OP hydrolase activity. The latter is important for both resistance and bioremediation because it enables the enzyme to recover its MCE activity after phosphorylation/inhibition by the 'activated' or 'P=O' form of OP insecticides. P=O OPs are encountered in an insect because they are generated by an insect's metabolism. For bioremediation the OP hydrolase is required for two reasons; firstly, to hydrolyse general OPs where these are the main contaminant, and secondly, to ensure that malathion hydrolysis by the enzyme will continue in the presence of minor contamination with 'P=O' OPs.

Allelism of the Malathion and Diazinon/Parathion Resistance Phenotypes in *L. Cuprina*

It is clear from the above molecular genetic and biochemical data that malathion resistance in *L. cuprina* is conferred by a structural mutation in the active site of LcαE7 (esterase E3), the same gene that is involved in resistance to diazinon/parathion type OPs. However, two classical genetic studies have detected a small number of presumptive recombinants between the malathion and diazinon resistance phenotypes in *L. cuprina*, which would suggest that they are separate, albeit closely linked, genes (Raftos, D. A. and Hughes, P. B., Journal of Economic Entomology 77: 553, 1986; Smyth, K-A., Russell, R. J. and Oakeshott, J. G., Biochemical Genetics 32: 437, 1994).

The availability of frozen extracts from three of the five presumptive recombinants generated by the study of Smyth et al. (1994) enabled the authors to test them directly for the predicted genotypes using PCR techniques. In this particular study, diazinon resistant males (strain Q4) were crossed to malathion resistant females (strain RM-8) and the F1 females backcrossed to Q4 males. Progeny were scored for the E3-non-staining, high MCE phenotypes as indicative of resistance to both diazinon and malathion. Five presumably recombinant individuals showing the MCE high/E3 non-staining phenotype were recovered from 692 backcross progeny; none were recovered with the reciprocal MCE low/E3 staining phenotype, which would presumably be susceptible to both malathion and diazinon.

Methods:

The regions of the LcαE7 gene surrounding the diazinon resistance (Gly to Asp substitution at position 137) and malathion resistance (Trp to Leu at position 251) mutations were amplified from each of the three available extracts from the Smyth et al., (1994) study, using the 7F1/7R2 and 7F7/7R4 primer sets, respectively. The PCR conditions and primers (except 7F7) are as described above, except that an annealing temperature of 55° C. and a buffer supplied by the manufacturer of Taq DNA polymerase (BRL; 0.2 mM of each dNTP, 20 mM Tris-HCl, pH8.4, 50 mM KCl, 1.5 mM MgCl$_2$) were used. The 7F7 primer has the sequence:5' tgctgcctctacccactacat 3í and its 5' position in the Lc743 sequence is nucleotide 660 (see FIG. 1).

The 330nt fragment of LcαE7 generated by the 7F7/7R4 primer set contains an RFLP polymorphism specific for each of the Q4 and RM-8 alleles: an NcoI cleavage site at nucleotide position 752 marks the Q4 allele (this polymorphism is at the site of the Trp to Leu mutation responsible for malathion resistance), while a BglI site at position 796 characterises the RM-8 allele. Therefore, in order to identify the Q4 and RM-8 alleles in each extract, PCR products were digested directly with each restriction enzyme and the products sized by agarose gel electrophoresis, using standard techniques (Sambrook, J., Fritsch. E. F. and Maniatis, T., Molecular Cloning: A Laboratory Manual, Second Edition, Cold Spring Harbor Laboratory Press, USA, 1989). Controls contained PCR products generated from Q4 and RM-8 genomic DNA.

No such convenient RFLP polymorphisms were contained in the 326nt fragment amplified by the 7F1/7R2 primer set (this fragment contains a 68nt intron at nucleotide position 360). However, three nucleotide polymorphisms distinguish the Q4 and RM-8 fragments: an A to T substitution at nucleotide position 303, T to C at position 345 and G to A at position 410 in the Q4 sequence (the latter substitution is responsible for diazinon/parathion resistance). PCR products were therefore cloned into the pGEM-T vector (Promega) using standard techniques (Sambrook, J., Fritsch. E. F. and Maniatis, T., Molecular Cloning: A Laboratory Manual, Second Edition, Cold Spring Harbor Laboratory Press, USA, 1989) and individual clones sequenced using commercially available SP6 and T7 primers and dye terminator technology, as described above.

Results:

Digestion of the PCR products generated by the 7F7/7R4 primer set with either Nco1 or Bgl1 revealed the presence of only the RM-8 chromosome in all three extracts (ie PCR products could be cleaved by Bgl1 and not Nco1, whereas the products of the control Q4 genomic DNA were readily digested with Nco1; data not shown). Curiously, the Q4 allele was not amplified from any of the extracts despite the fact that F1 progeny were backcrossed to Q4 in the crossing regime.

Two out of three clones derived from the first extract, and two out of two clones derived from a second, contained polymorphisms characteristic of the Q4 allele at positions 303 and 345 and the polymorphism characteristic of RM-8 at position 410. On the other hand, the third clone derived from the first extract and a single clone derived from the third extract contained all three polymorphisms characteristic of RM-8. Again, no fragments generated entirely from the Q4 chromosome were found among the cloned DNAs.

Conclusions:
1. The Q4 allele was not amplified from any of the extracts despite the fact that F1 progeny were backcrossed to Q4 and would therefore be expected to contain at least one copy of the Q4 fourth chromosome.
2. Progeny homozygous for the Q4 allele would be expected if the malathion resistance mutation was located on a gene separate from LcαE7. No such progeny were found.
3. No MCE low/E3 staining (presumably susceptible to both malathion and diazinon) progeny were recovered, which would be expected if E3 and MCE were separate genes.
4. At least two of the extracts contained a fourth chromosome that was a Q4/RM-8 recombinant somewhere in the region of the LcαE7 gene 5' to the Gly to Asp mutation at nucleotide position 410. The origin of flies carrying this fourth chromosome and the MCE activity/PAGE phenotype of the resultant chimeric protein are unknown.
5. It is clear that none of the putative E3/MCE recombinants were the outcome of simple reciprocal recombination events during the crossing programs; they do not, therefore, constitute proof that the E3 and MCE genes are separate genes.

It is clear from the present invention that malathion resistance in L. cuprina is the result of a structural mutation in the LcαE7 (E3) gene, the same gene which mutates to give resistance to diazinon/parathion type OPs. In other words, the MCE and E3 genes are probably allelic and not separated by 0.7 map units as previous classical genetic studies had indicated. The allelism of the two resistance mutations explains the observation of Smyth, K-A.,Russell, R. J. and Oakeshott,J. G. (Biochemical Genetics 32:437, 1994) that there is a negative association between malathion-type OP resistance and diazinon/parathion type OP resistance. The presence of malathion-type resistance alleles in a population would therefore suggest the use of diethyl OPs for combating flystrike, while the presence of diazinon/parathion-type resistance alleles would suggest the use of dimethyl OPs.

The MCE enzyme produced by the method of the present invention may be used to develop a functional in vitro assay for the degradation of carboxylester and dimethyl type OPs in much the same way as the E3 enzyme (Patent: Enzyme Based Bioremediation) has been used to develop an in vitro assay for the general OP hydrolysis. Used together, such assays provide scope for screening for alternative OPs that might overcome resistance problems by E3-like enzymes.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An isolated DNA molecule encoding an enzyme capable of hydrolyzing at least one organophosphate selected from the group consisting of carboxylester organophosphates and dimethyl-oxon organophosphates, the DNA molecule comprising a nucleotide sequence having at least 60% homology with LcαE7 (SEQ ID NO:7), in which the protein encoded by the DNA molecule differs from E3 (SEQ ID NO:8) at least in the substitution of Trp at position 251 with an amino acid selected from the group consisting of Leu, Ser, Ala, Ile, Val, Thr, Cys, Met and Gly.

2. An isolated DNA molecule as claimed in claim 1 in which the DNA molecule has at least 80% homology with the DNA encoding E3 (SEQ ID NO:8).

3. An isolated DNA molecule as claimed in claim 1 or claim 2 in which the DNA molecule has at least 95% homology with the DNA encoding E3 (SEQ ID NO:8).

4. An isolated DNA molecule as claimed in claim 1 in which the isolated DNA molecule has the nucleotide sequence of SEQ ID NOS:1, 3 or 5, or a sequence which hybridizes thereto with the proviso that the protein encoded by the DNA molecule differs from E3 (SEQ ID NO:8) at least in the substitution of Trp at position 251 with an amino acid selected from the group consisting of Leu, Ser, Ala, Ile, Val, Thr, Cys, Met and Gly.

5. An isolated DNA molecule as claimed in claim 1 in which the Trp at position 251 is substituted with Leu or Ser.

6. An isolated DNA molecule, the DNA molecule encoding a polypeptide having the amino acid sequence encoded by SEQ ID NO:9 RM-8Con or the amino acid sequence of MdαE7 SEQ ID NO:13 in which Trp at position 251 is replaced with Ser.

7. A transformed cell which expresses an enzyme capable of hydrolyzing at least one organophosphate selected from the group consisting of carboxylester organophosphates and dimethyl-oxon organophosphates, in which the cell is transformed with a DNA molecule as claimed in claim 1.

8. A transformed cell as claimed in claim 7 in which the cell is a prokaryotic cell or an insect cell.

9. A method of producing an enzyme capable of hydrolyzing at least one organophosphate selected from the group consisting of carboxylester organophosphates and dimethyl-oxon organophosphates, or an enzymatically active portion thereof, the method comprising transforming a host cell with the DNA molecule as claimed in claim 1 operatively linked to a control sequence, culturing the transformed cell under conditions which allow expression of the DNA sequence and recovering the produced enzyme, or enzymatically active portion thereof.

* * * * *

SEQUENCE LISTING

```
<160> NUMBER OF SEQ ID NOS: 43

<210> SEQ ID NO 1
<211> LENGTH: 1713
<212> TYPE: DNA
<213> ORGANISM: Lucilia cuprina

<400> SEQUENCE: 1
atgaatttca acgttagttt gatggagaaa ttaaaatgga agattaaatg cattgaaaat      60 aagttttaa actatcgttt aactaccaat gaaacgtgg tagctgaaac tgaatatggc      120
aaagtgaaag gcgttaaacg tttaactgtg tacgatgatt cctactacag ttttgagggt      180
ataccgtacg cccaaccgcc agtgggtgag ctgagattta aagcacccca gcgaccaaca      240
ccctgggatg gtgtgcgtga ttgttgcaat cataaagata agtcagtgca agttgatttt      300
ataacgggca aagtgtgtgg ctcagaggat tgtctatacc taagtgtcta tacgaataat      360
ctaaatcccg aaactaaacg tcccgtttta gtatacatac atggtggtgg ttttattatc      420
ggtgaaaatc atcgtgatat gtatggtcct gattatttca ttaaaaagga tgtggtgttg      480
```

-continued

```
attaacatac aatatcgttt gggagctcta ggtttctaa gtttaaattc agaagaccttt   540 aatgtgcccg gtaatgccgg ccttaaagat caagtcatgg ccttgcgttg gattaaaaat   600
aattgcgcca actttggtgg caatcccgat aatattacag tctttggtga agtgccggt    660 gctgcctcta cccactacat gatgttaacc gaacaaactc gcggtctttt ccatcgtggt   720
atactaatgt cgggtaatgc tatttgtcca ttggctaata cccaatgtca acatcgtgcc   780
ttcaccttag ccaaattggc cggctataag ggtgaggata atgataagga tgttttggaa   840
tttcttatga aagccaagcc acaggattta ataaaacttg aggaaaaagt tttaactcta   900
gaagagcgta caaataaggt catgtttcct tttggtccca ctgttgagcc atatcagacc   960
gctgattgtg tcttacccaa acatcctcgg gaaatggtta aaactgcttg ggtaattcg   1020 atacccacta tgatgggtaa cacttcatat gagggtctat ttttcacttc aattcttaag   1080
caaatgccta tgcttgttaa ggaattggaa acttgtgtca attttgtgcc aagtgaattg   1140
gctgatgttg aacgcaccgc cccagagacc ttggaaatgg gtgctaaaat taaaaaggct   1200
catgttacag gagaaacacc aacagctgat aatttttatgg atctttgctc tcacatctat   1260
ttctggttcc ccatgcatcg tttgttgcaa ttacgtttca atcacacctc cggtacaccc   1320
gtctacttgt atcgcttcga cttcgattcg gaagatctta tcaatcccta tcgtattatg   1380
cgtagtggac gtggtgttaa gggtgttagt catgctgatg aattaaccta tttcttctgg   1440
aatcaattgg ccaaacgtat gcctaaagaa tcgcgtgaat acaaaacaat tgaacgtatg   1500
actggtatat ggatacaatt tgccaccact ggtaatcctt atagcaatga aattgaaggt   1560
atggaaaatg tttcctggga tccaattaag aaatccgatg aagtatacaa gtgtttgaat   1620
attagtgatg aattgaaaat gattgatgtg cctgaaatgg ataagattaa acaatgggag   1680
tcgatgtttg aaaaacatag agatttattt tag                               1713
```

<210> SEQ ID NO 2
<211> LENGTH: 570
<212> TYPE: PRT
<213> ORGANISM: Lucilia cuprina

<400> SEQUENCE: 2

```
Met Asn Phe Asn Val Ser Leu Met Glu Lys Leu Lys Trp Lys Ile Lys
 1               5                  10                  15

Cys Ile Glu Asn Lys Phe Leu Asn Tyr Arg Leu Thr Thr Asn Glu Thr
             20                  25                  30

Val Val Ala Glu Thr Glu Tyr Gly Lys Val Lys Gly Val Lys Arg Leu
         35                  40                  45

Thr Val Tyr Asp Asp Ser Tyr Tyr Ser Phe Glu Gly Ile Pro Tyr Ala
     50                  55                  60

Gln Pro Pro Val Gly Glu Leu Arg Phe Lys Ala Pro Gln Arg Pro Thr
 65                  70                  75                  80

Pro Trp Asp Gly Val Arg Asp Cys Cys Asn His Lys Asp Lys Ser Val
                 85                  90                  95

Gln Val Asp Phe Ile Thr Gly Lys Val Cys Gly Ser Glu Asp Cys Leu
            100                 105                 110

Tyr Leu Ser Val Tyr Thr Asn Asn Leu Asn Pro Glu Thr Lys Arg Pro
        115                 120                 125

Val Leu Val Tyr Ile His Gly Gly Gly Phe Ile Ile Gly Glu Asn His
    130                 135                 140

Arg Asp Met Tyr Gly Pro Asp Tyr Phe Ile Lys Lys Asp Val Val Leu
145                 150                 155                 160
```

```
Ile Asn Ile Gln Tyr Arg Leu Gly Ala Leu Gly Phe Leu Ser Leu Asn
            165                 170                 175

Ser Glu Asp Leu Asn Val Pro Gly Asn Ala Gly Leu Lys Asp Gln Val
            180                 185                 190

Met Ala Leu Arg Trp Ile Lys Asn Asn Cys Ala Asn Phe Gly Gly Asn
            195                 200                 205

Pro Asp Asn Ile Thr Val Phe Gly Glu Ser Ala Gly Ala Ala Ser Thr
            210                 215                 220

His Tyr Met Met Leu Thr Glu Gln Thr Arg Gly Leu Phe His Arg Gly
225                 230                 235                 240

Ile Leu Met Ser Gly Asn Ala Ile Cys Pro Leu Ala Asn Thr Gln Cys
                245                 250                 255

Gln His Arg Ala Phe Thr Leu Ala Lys Leu Ala Gly Tyr Lys Gly Glu
                260                 265                 270

Asp Asn Asp Lys Asp Val Leu Glu Phe Leu Met Lys Ala Lys Pro Gln
                275                 280                 285

Asp Leu Ile Lys Leu Glu Glu Lys Val Leu Thr Leu Glu Glu Arg Thr
            290                 295                 300

Asn Lys Val Met Phe Pro Phe Gly Pro Thr Val Glu Pro Tyr Gln Thr
305                 310                 315                 320

Ala Asp Cys Val Leu Pro Lys His Pro Arg Glu Met Val Lys Thr Ala
                325                 330                 335

Trp Gly Asn Ser Ile Pro Thr Met Met Gly Asn Thr Ser Tyr Glu Gly
                340                 345                 350

Leu Phe Phe Thr Ser Ile Leu Lys Gln Met Pro Met Leu Val Lys Glu
                355                 360                 365

Leu Glu Thr Cys Val Asn Phe Val Pro Ser Glu Leu Ala Asp Ala Glu
            370                 375                 380

Arg Thr Ala Pro Glu Thr Leu Glu Met Gly Ala Lys Ile Lys Lys Ala
385                 390                 395                 400

His Val Thr Gly Glu Thr Pro Thr Ala Asp Asn Phe Met Asp Leu Cys
                405                 410                 415

Ser His Ile Tyr Phe Trp Phe Pro Met His Arg Leu Leu Gln Leu Arg
                420                 425                 430

Phe Asn His Thr Ser Gly Thr Pro Val Tyr Leu Tyr Arg Phe Asp Phe
            435                 440                 445

Asp Ser Glu Asp Leu Ile Asn Pro Tyr Arg Ile Met Arg Ser Gly Arg
            450                 455                 460

Gly Val Lys Gly Val Ser His Ala Asp Glu Leu Thr Tyr Phe Phe Trp
465                 470                 475                 480

Asn Gln Leu Ala Lys Arg Met Pro Lys Glu Ser Arg Glu Tyr Lys Thr
                485                 490                 495

Ile Glu Arg Met Thr Gly Ile Trp Ile Gln Phe Ala Thr Thr Gly Asn
                500                 505                 510

Pro Tyr Ser Asn Glu Ile Glu Gly Met Glu Asn Val Ser Trp Asp Pro
            515                 520                 525

Ile Lys Lys Ser Asp Glu Val Tyr Lys Cys Leu Asn Ile Ser Asp Glu
            530                 535                 540

Leu Lys Met Ile Asp Val Pro Glu Met Asp Lys Ile Lys Gln Trp Glu
545                 550                 555                 560

Ser Met Phe Glu Lys His Arg Asp Leu Phe
                565                 570
```

<210> SEQ ID NO 3
<211> LENGTH: 1713
<212> TYPE: DNA
<213> ORGANISM: Lucilia cuprina

<400> SEQUENCE: 3

| | | | | | |
|---|---|---|---|---|---|
| atgaatttca | acgttagttt | gatggagaaa | ttaaaatgga | agattaaatg | cattgaaaat | 60 |
| aagttttaa | actatcgttt | aactaccaat | gaaacggtgg | tagctgaaac | tgaatatggc | 120 |
| aaagtgaaag | gcgttaaacg | tttaactgtg | tacgatgatt | cctactacag | ttttgagggt | 180 |
| ataccgtacg | cccaaccgcc | agtgggtgag | ctgagattta | aagcacccca | gcgaccaaca | 240 |
| ccctgggatg | tgtgcgcga | ttgttgcaat | cataaagata | agtcagtgca | agttgatttt | 300 |
| ataacgggca | aagtgtgtgg | ctcagaggat | tgtctatacc | taagtgtcta | tacgaataat | 360 |
| ctaaatcccg | aaactaaacg | tcccgtttta | gtatacatac | atggtggtgg | ttttattatc | 420 |
| ggtgaaaatc | atcgtgatat | gtatggtcct | gattatttca | ttaaaaagga | tgtggtgttg | 480 |
| attaacatac | aatatcgttt | gggagctcta | gttttctaa | gtttaaattc | agaagacctt | 540 |
| aatgtgcccg | gtaatgccgg | ccttaaagat | caagtcatgg | ccttgcgttg | gattaaaaat | 600 |
| aattgcgcca | actttggtgg | caatcccgat | aatattacag | tctttggtga | agtgccggt | 660 |
| gctgcctcta | cccactacat | gatgttaacc | gaacaaactc | gcggtctttt | ccatcgtggt | 720 |
| atactaatgt | cgggtaatgc | tatttgtcca | ttggctaata | cccaatgtca | acatcgtgcc | 780 |
| ttcaccttag | ccaaattggc | cggctataag | ggtgaggata | atgataagga | tgttttggaa | 840 |
| tttcttatga | agccaagcc | acaggattta | ataaaacttg | aggaaaaagt | tttaactcta | 900 |
| gaagagcgta | caaataaggt | catgtttcct | tttggtccca | ctgttgagcc | atatcagacc | 960 |
| gctgattgtg | tcttacccaa | acatcctcgg | gaaatggtta | aaactgcttg | gggtaattcg | 1020 |
| atacccacta | tgatgggtaa | cacttcatat | gagggtctat | ttttcacttc | aattcttaag | 1080 |
| caaatgccta | tgcttgttaa | ggaattggaa | acttgtgtca | attttgtgcc | aagtgaattg | 1140 |
| gctgatgctg | aacgcaccgc | cccagagacc | ttggaaatgg | gtgctaaaat | taaaaaggct | 1200 |
| catgttacag | gagaaacacc | aacagctgat | aattttatgg | atctttgctc | tcacatctat | 1260 |
| ttctggttcc | ccatgcatcg | tttgttgcaa | ttacgtttca | atcacacctc | cggtacaccc | 1320 |
| gtctacttgt | atcgcttcga | cttcgattcg | gaagatctta | tcaatcccta | tcgtattatg | 1380 |
| cgtagtggac | gtggtgttaa | gggtgttagt | catgctgatg | aattaaccta | tttcttctgg | 1440 |
| aatcaattgg | ccaaacgtat | gcctaaagaa | tcgcgtgaat | acaaaacaat | tgaacgtatg | 1500 |
| actggtatat | ggatacaatt | tgccaccact | ggtaatcctt | atagcaatga | aattgaaggt | 1560 |
| atggaaaatg | tttcctggga | tccaattaag | aaatccgatg | aagtatacaa | gtgtttgaat | 1620 |
| attagtgatg | aattgaaaat | gattgatgtg | cctgaaatgg | ataagattaa | acaatgggag | 1680 |
| tcgatgtttg | aaaaacatag | agatttattt | tag | | | 1713 |

<210> SEQ ID NO 4
<211> LENGTH: 570
<212> TYPE: PRT
<213> ORGANISM: Lucilia cuprina

<400> SEQUENCE: 4

Met Asn Phe Asn Val Ser Leu Met Glu Lys Leu Lys Trp Lys Ile Lys
 1               5                  10                  15

Cys Ile Glu Asn Lys Phe Leu Asn Tyr Arg Leu Thr Thr Asn Glu Thr
            20                  25                  30

-continued

```
Val Val Ala Glu Thr Glu Tyr Gly Lys Val Lys Gly Val Lys Arg Leu
         35                  40                  45
Thr Val Tyr Asp Asp Ser Tyr Tyr Ser Phe Glu Gly Ile Pro Tyr Ala
     50                  55                  60
Gln Pro Pro Val Gly Glu Leu Arg Phe Lys Ala Pro Gln Arg Pro Thr
 65                  70                  75                  80
Pro Trp Asp Gly Val Arg Asp Cys Cys Asn His Lys Asp Lys Ser Val
                 85                  90                  95
Gln Val Asp Phe Ile Thr Gly Lys Val Cys Gly Ser Glu Asp Cys Leu
                100                 105                 110
Tyr Leu Ser Val Tyr Thr Asn Asn Leu Asn Pro Glu Thr Lys Arg Pro
        115                 120                 125
Val Leu Val Tyr Ile His Gly Gly Phe Ile Ile Gly Glu Asn His
    130                 135                 140
Arg Asp Met Tyr Gly Pro Asp Tyr Phe Ile Lys Lys Asp Val Val Leu
145                 150                 155                 160
Ile Asn Ile Gln Tyr Arg Leu Gly Ala Leu Gly Phe Leu Ser Leu Asn
                165                 170                 175
Ser Glu Asp Leu Asn Val Pro Gly Asn Ala Gly Leu Lys Asp Gln Val
            180                 185                 190
Met Ala Leu Arg Trp Ile Lys Asn Asn Cys Ala Asn Phe Gly Gly Asn
        195                 200                 205
Pro Asp Asn Ile Thr Val Phe Gly Glu Ser Ala Gly Ala Ala Ser Thr
    210                 215                 220
His Tyr Met Met Leu Thr Glu Gln Thr Arg Gly Leu Phe His Arg Gly
225                 230                 235                 240
Ile Leu Met Ser Gly Asn Ala Ile Cys Pro Leu Ala Asn Thr Gln Cys
                245                 250                 255
Gln His Arg Ala Phe Thr Leu Ala Lys Leu Ala Gly Tyr Lys Gly Glu
            260                 265                 270
Asp Asn Asp Lys Asp Val Leu Glu Phe Leu Met Lys Ala Lys Pro Gln
        275                 280                 285
Asp Leu Ile Lys Leu Glu Glu Lys Val Leu Thr Leu Glu Glu Arg Thr
    290                 295                 300
Asn Lys Val Met Phe Pro Phe Gly Pro Thr Val Glu Pro Tyr Gln Thr
305                 310                 315                 320
Ala Asp Cys Val Leu Pro Lys His Pro Arg Glu Met Val Lys Thr Ala
                325                 330                 335
Trp Gly Asn Ser Ile Pro Thr Met Met Gly Asn Thr Ser Tyr Glu Gly
            340                 345                 350
Leu Phe Phe Thr Ser Ile Leu Lys Gln Met Pro Met Leu Val Lys Glu
        355                 360                 365
Leu Glu Thr Cys Val Asn Phe Val Pro Ser Glu Leu Ala Asp Ala Glu
    370                 375                 380
Arg Thr Ala Pro Glu Thr Leu Glu Met Gly Ala Lys Ile Lys Lys Ala
385                 390                 395                 400
His Val Thr Gly Glu Thr Pro Thr Ala Asp Asn Phe Met Asp Leu Cys
                405                 410                 415
Ser His Ile Tyr Phe Trp Phe Pro Met His Arg Leu Leu Gln Leu Arg
            420                 425                 430
Phe Asn His Thr Ser Gly Thr Pro Val Tyr Leu Tyr Arg Phe Asp Phe
        435                 440                 445
```

```
Asp Ser Glu Asp Leu Ile Asn Pro Tyr Arg Ile Met Arg Ser Gly Arg
        450                 455                 460

Gly Val Lys Gly Val Ser His Ala Asp Glu Leu Thr Tyr Phe Phe Trp
465                 470                 475                 480

Asn Gln Leu Ala Lys Arg Met Pro Lys Glu Ser Arg Glu Tyr Lys Thr
                485                 490                 495

Ile Glu Arg Met Thr Gly Ile Trp Ile Gln Phe Ala Thr Thr Gly Asn
                500                 505                 510

Pro Tyr Ser Asn Glu Ile Glu Gly Met Glu Asn Val Ser Trp Asp Pro
                515                 520                 525

Ile Lys Lys Ser Asp Glu Val Tyr Lys Cys Leu Asn Ile Ser Asp Glu
                530                 535                 540

Leu Lys Met Ile Asp Val Pro Glu Met Asp Lys Ile Lys Gln Trp Glu
545                 550                 555                 560

Ser Met Phe Glu Lys His Arg Asp Leu Phe
                565                 570

<210> SEQ ID NO 5
<211> LENGTH: 1713
<212> TYPE: DNA
<213> ORGANISM: Lucilia cuprina

<400> SEQUENCE: 5
atgaatttca acgttagttt gatggagaaa ttaaaatgga agattaaatg cattgaaaat      60
aagtttttaa actatcgttt aactaccaat gaaacggtgg tagctgaaac tgaatatggc     120
aaagtgaaag gcgttaaacg tttaactgtg tacgatgatt cctactacag ttttgagggt     180
ataccgtacg cccaaccgcc agtgggtgag ctgagattta aagcacccca gcgaccaaca     240
ccctgggatg gtgtgcgtga ttgttgcaat cataaagata agtcagtgca agttgatttt     300
ataacgggca aagtgtgtgg ctcagaggat tgtctatacc taagtgtcta tacgaataat     360
ctaaatcccg aaactaaacg tcccgtttta gtatacatac atggtggtgg ttttattatc     420
ggtgaaaatc atcgtgatat gtatggtcct gattatttca ttaaaaagga tgtggtgttg     480
attaacatac aatatcgttt gggagctcta ggttttctaa gtttaaattc agaagacctt     540
aatgtgcccg gtaatgccgg ccttaaagat caagtcatgg ccttgcattg gattaaaaat     600
aattgcgcca actttggtgg caatcccgat aatattacag tctttggtga agtgccggt      660 gctgcctcta cccactacat gatgttaacc gaacaaactc gcggtctttt ccatcgtggt     720
atactaatgt cgggtaatgc tatttgtcca ttggctaata cccaatgtca acatcgtgcc     780
ttcaccttag ccaaattggc cggctataag ggtgagaata atgataagga tgttttggaa     840
tttcttatga agccaagcc acaggattta gtaaaacttg aggaaaaagt tttaactcta     900
gaagagcgta caaataaggt catgtttcct tttggtccca ctgttgagcc atatcagacc     960
gctgattgtg tcttacccaa acatcctcgg gaaatggtta aaactgcttg gggtaattcg    1020
atacccacta tgatgggtaa cacttcatat gagggtctat ttttcacttc aattcttaag    1080
caaatgccta tgcttgttaa ggaattggaa acttgtgtca attttgtgcc aagtgaattg    1140
gctgatgctg aacgcaccgc cccagagacc ttggaaatgg gtgctaaaat taaaaaggct    1200
catgttacag gagaaacacc aacagctgat aattttatgg atctttgctc tcacatctat    1260
ttctggttcc ccatgcatcg tttgttgcaa ttacgtttca atcacacctc cggtacaccc    1320
gtctacttgt atcgcttcga cttcgattcg gaagatctta tcaatcccta tcgtattatg    1380
cgtagtggac gtggtgttaa gggtgttagt catgctgatg aattaaccta tttcttctgg    1440
```

```
aatcaattgg ccaaacgtat gcctaaagaa tcgcgtgaat acaaaacaat tgaacgtatg    1500
actggtatat ggatacaatt tgccaccact ggtaatcctt atagcaatga aattgaaggt    1560
atggaaaatg tttcctggga tccaattaag aaatccgatg aagtatacaa gtgtttgaat    1620
attagtgatg aattgaaaat gattgatgtg cctgaaatgg ataagattaa acaatgggag    1680
tcgatgtttg aaaaacatag agatttattt tag                                1713
```

<210> SEQ ID NO 6
<211> LENGTH: 570
<212> TYPE: PRT
<213> ORGANISM: Lucilia cuprina

<400> SEQUENCE: 6

```
Met Asn Phe Asn Val Ser Leu Met Glu Lys Leu Lys Trp Lys Ile Lys
  1               5                  10                  15

Cys Ile Glu Asn Lys Phe Leu Asn Tyr Arg Leu Thr Thr Asn Glu Thr
             20                  25                  30

Val Val Ala Glu Thr Glu Tyr Gly Lys Val Lys Gly Val Lys Arg Leu
         35                  40                  45

Thr Val Tyr Asp Asp Ser Tyr Tyr Ser Phe Glu Gly Ile Pro Tyr Ala
     50                  55                  60

Gln Pro Pro Val Gly Glu Leu Arg Phe Lys Ala Pro Gln Arg Pro Thr
 65                  70                  75                  80

Pro Trp Asp Gly Val Arg Asp Cys Cys Asn His Lys Asp Lys Ser Val
                 85                  90                  95

Gln Val Asp Phe Ile Thr Gly Lys Val Cys Gly Ser Glu Asp Cys Leu
            100                 105                 110

Tyr Leu Ser Val Tyr Thr Asn Asn Leu Asn Pro Glu Thr Lys Arg Pro
        115                 120                 125

Val Leu Val Tyr Ile His Gly Gly Phe Ile Ile Gly Glu Asn His
    130                 135                 140

Arg Asp Met Tyr Gly Pro Asp Tyr Phe Ile Lys Lys Asp Val Val Leu
145                 150                 155                 160

Ile Asn Ile Gln Tyr Arg Leu Gly Ala Leu Gly Phe Leu Ser Leu Asn
                165                 170                 175

Ser Glu Asp Leu Asn Val Pro Gly Asn Ala Gly Leu Lys Asp Gln Val
            180                 185                 190

Met Ala Leu Arg Trp Ile Lys Asn Asn Cys Ala Asn Phe Gly Gly Asn
        195                 200                 205

Pro Asp Asn Ile Thr Val Phe Gly Glu Ser Ala Gly Ala Ala Ser Thr
    210                 215                 220

His Tyr Met Met Leu Thr Glu Gln Thr Arg Gly Leu Phe His Arg Gly
225                 230                 235                 240

Ile Leu Met Ser Gly Asn Ala Ile Cys Pro Leu Ala Asn Thr Gln Cys
                245                 250                 255

Gln His Arg Ala Phe Thr Leu Ala Lys Leu Ala Gly Tyr Lys Gly Glu
            260                 265                 270

Asp Asn Asp Lys Asp Val Leu Glu Phe Leu Met Lys Ala Lys Pro Gln
        275                 280                 285

Asp Leu Ile Lys Leu Glu Glu Lys Val Leu Thr Leu Glu Glu Arg Thr
    290                 295                 300

Asn Lys Val Met Phe Pro Phe Gly Pro Thr Val Glu Pro Tyr Gln Thr
305                 310                 315                 320
```

```
Ala Asp Cys Val Leu Pro Lys His Pro Arg Glu Met Val Lys Thr Ala
            325                 330                 335

Trp Gly Asn Ser Ile Pro Thr Met Met Gly Asn Thr Ser Tyr Glu Gly
            340                 345                 350

Leu Phe Phe Thr Ser Ile Leu Lys Gln Met Pro Met Leu Val Lys Glu
            355                 360                 365

Leu Glu Thr Cys Val Asn Phe Val Pro Ser Glu Leu Ala Asp Ala Glu
            370                 375                 380

Arg Thr Ala Pro Glu Thr Leu Glu Met Gly Ala Lys Ile Lys Lys Ala
385                 390                 395                 400

His Val Thr Gly Glu Thr Pro Thr Ala Asp Asn Phe Met Asp Leu Cys
            405                 410                 415

Ser His Ile Tyr Phe Trp Phe Pro Met His Arg Leu Leu Gln Leu Arg
            420                 425                 430

Phe Asn His Thr Ser Gly Thr Pro Val Tyr Leu Tyr Arg Phe Asp Phe
            435                 440                 445

Asp Ser Glu Asp Leu Ile Asn Pro Tyr Arg Ile Met Arg Ser Gly Arg
            450                 455                 460

Gly Val Lys Gly Val Ser His Ala Asp Glu Leu Thr Tyr Phe Phe Trp
465                 470                 475                 480

Asn Gln Leu Ala Lys Arg Met Pro Lys Glu Ser Arg Glu Tyr Lys Thr
            485                 490                 495

Ile Glu Arg Met Thr Gly Ile Trp Ile Gln Phe Ala Thr Thr Gly Asn
            500                 505                 510

Pro Tyr Ser Asn Glu Ile Glu Gly Met Glu Asn Val Ser Trp Asp Pro
            515                 520                 525

Ile Lys Lys Ser Asp Glu Val Tyr Lys Cys Leu Asn Ile Ser Asp Glu
            530                 535                 540

Leu Lys Met Ile Asp Val Pro Glu Met Asp Lys Ile Lys Gln Trp Glu
545                 550                 555                 560

Ser Met Phe Glu Lys His Arg Asp Leu Phe
            565                 570

<210> SEQ ID NO 7
<211> LENGTH: 1713
<212> TYPE: DNA
<213> ORGANISM: Lucilia cuprina

<400> SEQUENCE: 7
atgaatttca acgttagttt gatggagaaa ttaaaatgga agattaaatg cattgaaaat      60
aagtttttaa actatcgttt aactaccaat gaaacggtgg tagctgaaac tgaatatggc     120
aaagtgaaag gcgttaaacg tttaactgtg tacgatgatt cctactacag ttttgagggt     180
ataccgtacg cccaaccgcc agtgggtgag ctgagattta aagcacccca gcgaccaaca     240
ccctgggatg gtgtgcgtga ttgttgcaat cataaagata agtcagtgca agttgatttt     300
ataacgggca agtgtgtggg ctcagaggat tgtctatacc taagtgtcta tacgaataat     360
ctaaatcccg aaactaaacg tcccgtttta gtatacatac atggtggtgg ttttattatc     420
ggtgaaaatc atcgtgatat gtatggtcct gattatttca ttaaaaagga tgtggtgttg     480
attaacatac aatatcgttt gggagctcta ggttttctaa gtttaaattc agaagacctt     540
aatgtgcccg gtaatgccgg ccttaaagat caagtcatgg ccttgcgttg gattaaaaat     600
aattgcgcca actttggtgg caatcccgat aatattacag tctttggtga agtgccggt      660 gctgcctcta cccactacat gatgttaacc gaacaaactc gcggtctttt ccatcgtggt     720
```

-continued

```
atactaatgt cgggtaatgc tatttgtcca tgggctaata cccaatgtca acatcgtgcc    780
ttcaccttag ccaaattggc cggctataag ggtgaggata atgataagga tgttttggaa    840
tttcttatga aagccaagcc acaggattta ataaaacttg aggaaaaagt tttaactcta    900
gaagagcgta caaataaggt catgtttcct tttggtccca ctgttgagcc atatcagacc    960
gctgattgtg tcttacccaa acatcctcgg gaaatggtta aaactgcttg gggtaattcg   1020
atacccacta tgatgggtaa cacttcatat gagggtctat ttttcacttc aattcttaag   1080
caaatgccta tgcttgttaa ggaattggaa acttgtgtca attttgtgcc aagtgaattg   1140
gctgatgctg aacgcaccgc cccagagacc ttggaaatgg gtgctaaaat taaaaaggct   1200
catgttacag gagaaacacc aacagctgat aattttatgg atctttgctc tcacatctat   1260
ttctggttcc ccatgcatcg tttgttgcaa ttacgtttca atcacacctc cggtacaccc   1320
gtctacttgt atcgcttcga ctttgattcg aagatcttat taatcccta tcgtattatg   1380
cgtagtggac gtggtgttaa gggtgttagt catgctgatg aattaaccta tttcttctgg   1440
aatcaattgg ccaaacgtat gcctaaagaa tcgcgtgaat acaaaacaat tgaacgtatg   1500
actggtatat ggatacaatt tgccaccact ggtaatcctt atagcaatga aattgaaggt   1560
atggaaaatg tttcctggga tccaattaag aaatccgacg aagtatacaa gtgtttgaat   1620
attagtgacg aattgaaaat gattgatgtg cctgaaatgg ataagattaa acaatgggaa   1680
tcgatgtttg aaaaacatag agatttattt tag                                1713

<210> SEQ ID NO 8
<211> LENGTH: 570
<212> TYPE: PRT
<213> ORGANISM: Lucilia cuprina

<400> SEQUENCE: 8

Met Asn Phe Asn Val Ser Leu Met Glu Lys Leu Lys Trp Lys Ile Lys
  1               5                  10                  15

Cys Ile Glu Asn Lys Phe Leu Asn Tyr Arg Leu Thr Thr Asn Glu Thr
             20                  25                  30

Val Val Ala Glu Thr Glu Tyr Gly Lys Val Lys Gly Val Lys Arg Leu
         35                  40                  45

Thr Val Tyr Asp Asp Ser Tyr Tyr Ser Phe Glu Gly Ile Pro Tyr Ala
     50                  55                  60

Gln Pro Pro Val Gly Glu Leu Arg Phe Lys Ala Pro Gln Arg Pro Thr
 65                  70                  75                  80

Pro Trp Asp Gly Val Arg Asp Cys Cys Asn His Lys Asp Lys Ser Val
                 85                  90                  95

Gln Val Asp Phe Ile Thr Gly Lys Val Cys Gly Ser Glu Asp Cys Leu
            100                 105                 110

Tyr Leu Ser Val Tyr Thr Asn Asn Leu Asn Pro Glu Thr Lys Arg Pro
        115                 120                 125

Val Leu Val Tyr Ile His Gly Gly Phe Ile Ile Gly Glu Asn His
    130                 135                 140

Arg Asp Met Tyr Gly Pro Asp Tyr Phe Ile Lys Lys Asp Val Val Leu
145                 150                 155                 160

Ile Asn Ile Gln Tyr Arg Leu Gly Ala Leu Gly Phe Leu Ser Leu Asn
                165                 170                 175

Ser Glu Asp Leu Asn Val Pro Gly Asn Ala Gly Leu Lys Asp Gln Val
            180                 185                 190
```

```
Met Ala Leu Arg Trp Ile Lys Asn Asn Cys Ala Asn Phe Gly Gly Asn
        195                 200                 205

Pro Asp Asn Ile Thr Val Phe Gly Glu Ser Ala Gly Ala Ala Ser Thr
    210                 215                 220

His Tyr Met Met Leu Thr Glu Gln Thr Arg Gly Leu Phe His Arg Gly
225                 230                 235                 240

Ile Leu Met Ser Gly Asn Ala Ile Cys Pro Trp Ala Asn Thr Gln Cys
                245                 250                 255

Gln His Arg Ala Phe Thr Leu Ala Lys Leu Ala Gly Tyr Lys Gly Glu
            260                 265                 270

Asp Asn Asp Lys Asp Val Leu Glu Phe Leu Met Lys Ala Lys Pro Gln
        275                 280                 285

Asp Leu Ile Lys Leu Glu Glu Lys Val Leu Thr Leu Glu Glu Arg Thr
    290                 295                 300

Asn Lys Val Met Phe Pro Phe Gly Pro Thr Val Glu Pro Tyr Gln Thr
305                 310                 315                 320

Ala Asp Cys Val Leu Pro Lys His Pro Arg Glu Met Val Lys Thr Ala
                325                 330                 335

Trp Gly Asn Ser Ile Pro Thr Met Met Gly Asn Thr Ser Tyr Glu Gly
            340                 345                 350

Leu Phe Phe Thr Ser Ile Leu Lys Gln Met Pro Met Leu Val Lys Glu
        355                 360                 365

Leu Glu Thr Cys Val Asn Phe Val Pro Ser Glu Leu Ala Asp Ala Glu
    370                 375                 380

Arg Thr Ala Pro Glu Thr Leu Glu Met Gly Ala Lys Ile Lys Lys Ala
385                 390                 395                 400

His Val Thr Gly Glu Thr Pro Thr Ala Asp Asn Phe Met Asp Leu Cys
                405                 410                 415

Ser His Ile Tyr Phe Trp Phe Pro Met His Arg Leu Leu Gln Leu Arg
            420                 425                 430

Phe Asn His Thr Ser Gly Thr Pro Val Tyr Leu Tyr Arg Phe Asp Phe
        435                 440                 445

Asp Ser Glu Asp Leu Ile Asn Pro Tyr Arg Ile Met Arg Ser Gly Arg
    450                 455                 460

Gly Val Lys Gly Val Ser His Ala Asp Glu Leu Thr Tyr Phe Phe Trp
465                 470                 475                 480

Asn Gln Leu Ala Lys Arg Met Pro Lys Glu Ser Arg Glu Tyr Lys Thr
                485                 490                 495

Ile Glu Arg Met Thr Gly Ile Trp Ile Gln Phe Ala Thr Thr Gly Asn
            500                 505                 510

Pro Tyr Ser Asn Glu Ile Glu Gly Met Glu Asn Val Ser Trp Asp Pro
        515                 520                 525

Ile Lys Lys Ser Asp Glu Val Tyr Lys Cys Leu Asn Ile Ser Asp Glu
    530                 535                 540

Leu Lys Met Ile Asp Val Pro Glu Met Asp Lys Ile Lys Gln Trp Glu
545                 550                 555                 560

Ser Met Phe Glu Lys His Arg Asp Leu Phe
                565                 570

<210> SEQ ID NO 9
<211> LENGTH: 1713
<212> TYPE: DNA
<213> ORGANISM: Lucilia cuprina

<400> SEQUENCE: 9
```

-continued

```
atgaatttca acgttagttt gatggagaaa ttaaaatgga agattaaatg cattgaaaat      60 aagttttta actatcgttt aactaccaat gaaacggtgg tagctgaaac tgaatatggc     120
aaagtgaaag gcgttaaacg tttaactgtg tacgatgatt cctactacag ttttgagggt    180
ataccgtacg cccaaccgcc agtgggtgag ctgagattta aagcacccca gcgaccaaca    240
ccctgggatg gtgtgcgtga ttgttgcaat cataaagata agtcagtgca agttgatttt    300
ataacgggca aagtgtgtgg ctcagaggat tgtctatacc taagtgtcta tacgaataat    360
ctaaatcccg aaactaaacg tcccgtttta gtatacatac atggtggtgg ttttattatc    420
ggtgaaaatc atcgtgatat gtatggtcct gattatttca ttaaaaagga tgtggtgttg    480
attaacatac aatatcgttt gggagctcta ggttttctaa gtttaaattc agaagacctt    540
aatgtgcccg gtaatgccgg ccttaaagat caagtcatgg ccttgcgttg gattaaaaat    600
aattgcgcca actttggtgg caatcccgat aatattacag tctttggtga agtgccggt     660 gctgcctcta cccactacat gatgttaacc gaacaaactc gcggtctttt ccatcgtggt    720
atactaatgt cgggtaatgc tatttgtcca ttggctaata cccaatgtca acatcgtgcc    780
ttcaccttag ccaaattggc cggctataag ggtgaggata atgataagga tgttttggaa    840
tttcttatga aagccaagcc acaggattta ataaaacttg aggaaaaagt tttaactcta    900
gaagagcgta caaataaggt catgtttcct tttggtccca ctgttgagcc atatcagacc    960
gctgattgtg tcttacccaa acatcctcgg gaaatggtta aaactgcttg ggtaattcg    1020 atacccacta tgatgggtaa cacttcatat gagggtctat ttttcacttc aattcttaag   1080
caaatgccta tgcttgttaa ggaattggaa acttgtgtca attttgtgcc aagtgaattg   1140
gctgatgctg aacgcaccgc cccagagacc ttggaaatgg gtgctaaaat taaaaaggct   1200
catgttacag gagaaacacc aacagctgat aattttatgg atctttgctc tcacatctat   1260
ttctggttcc ccatgcatcg tttgttgcaa ttacgtttca atcacacctc cggtacaccc   1320
gtctacttgt atcgcttcga cttcgattcg gaagatctta tcaatcccta tcgtattatg   1380
cgtagtggac gtggtgttaa gggtgttagt catgctgatg aattaaccta tttcttctgg   1440
aatcaattgg ccaaacgtat gcctaaagaa tcgcgtgaat acaaaacaat tgaacgtatg   1500
actggtatat ggatacaatt tgccaccact ggtaatcctt atagcaatga aattgaaggt   1560
atggaaaatg tttcctggga tccaattaag aaatccgatg aagtatacaa gtgtttgaat   1620
attagtgatg aattgaaaat gattgatgtg cctgaaatgg ataagattaa acaatgggag   1680
tcgatgtttg aaaaacatag agatttattt tag                                1713
```

<210> SEQ ID NO 10
<211> LENGTH: 570
<212> TYPE: PRT
<213> ORGANISM: Lucilia cuprina

<400> SEQUENCE: 10

```
Met Asn Phe Asn Val Ser Leu Met Glu Lys Leu Lys Trp Lys Ile Lys
  1               5                  10                  15

Cys Ile Glu Asn Lys Phe Leu Asn Tyr Arg Leu Thr Thr Asn Glu Thr
             20                  25                  30

Val Val Ala Glu Thr Glu Tyr Gly Lys Val Lys Gly Val Lys Arg Leu
         35                  40                  45

Thr Val Tyr Asp Asp Ser Tyr Tyr Ser Phe Glu Gly Ile Pro Tyr Ala
     50                  55                  60
```

```
Gln Pro Pro Val Gly Glu Leu Arg Phe Lys Ala Pro Gln Arg Pro Thr
 65                  70                  75                  80

Pro Trp Asp Gly Val Arg Asp Cys Cys Asn His Lys Asp Lys Ser Val
                 85                  90                  95

Gln Val Asp Phe Ile Thr Gly Lys Val Cys Gly Ser Glu Asp Cys Leu
            100                 105                 110

Tyr Leu Ser Val Tyr Thr Asn Asn Leu Asn Pro Glu Thr Lys Arg Pro
        115                 120                 125

Val Leu Val Tyr Ile His Gly Gly Phe Ile Ile Gly Glu Asn His
    130                 135                 140

Arg Asp Met Tyr Gly Pro Asp Tyr Phe Ile Lys Lys Asp Val Val Leu
145                 150                 155                 160

Ile Asn Ile Gln Tyr Arg Leu Gly Ala Leu Gly Phe Leu Ser Leu Asn
                165                 170                 175

Ser Glu Asp Leu Asn Val Pro Gly Asn Ala Gly Leu Lys Asp Gln Val
            180                 185                 190

Met Ala Leu Arg Trp Ile Lys Asn Asn Cys Ala Asn Phe Gly Gly Asn
        195                 200                 205

Pro Asp Asn Ile Thr Val Phe Gly Glu Ser Ala Gly Ala Ala Ser Thr
210                 215                 220

His Tyr Met Met Leu Thr Glu Gln Thr Arg Gly Leu Phe His Arg Gly
225                 230                 235                 240

Ile Leu Met Ser Gly Asn Ala Ile Cys Pro Leu Ala Asn Thr Gln Cys
                245                 250                 255

Gln His Arg Ala Phe Thr Leu Ala Lys Leu Ala Gly Tyr Lys Gly Glu
            260                 265                 270

Asp Asn Asp Lys Asp Val Leu Glu Phe Leu Met Lys Ala Lys Pro Gln
        275                 280                 285

Asp Leu Ile Lys Leu Glu Glu Lys Val Leu Thr Leu Glu Glu Arg Thr
    290                 295                 300

Asn Lys Val Met Phe Pro Phe Gly Pro Thr Val Glu Pro Tyr Gln Thr
305                 310                 315                 320

Ala Asp Cys Val Leu Pro Lys His Pro Arg Glu Met Val Lys Thr Ala
                325                 330                 335

Trp Gly Asn Ser Ile Pro Thr Met Met Gly Asn Thr Ser Tyr Glu Gly
            340                 345                 350

Leu Phe Phe Thr Ser Ile Leu Lys Gln Met Pro Met Leu Val Lys Glu
        355                 360                 365

Leu Glu Thr Cys Val Asn Phe Val Pro Ser Glu Leu Ala Asp Ala Glu
    370                 375                 380

Arg Thr Ala Pro Glu Thr Leu Glu Met Gly Ala Lys Ile Lys Lys Ala
385                 390                 395                 400

His Val Thr Gly Glu Thr Pro Thr Ala Asp Asn Phe Met Asp Leu Cys
                405                 410                 415

Ser His Ile Tyr Phe Trp Phe Pro Met His Arg Leu Leu Gln Leu Arg
            420                 425                 430

Phe Asn His Thr Ser Gly Thr Pro Val Tyr Leu Tyr Arg Phe Asp Phe
        435                 440                 445

Asp Ser Glu Asp Leu Ile Asn Pro Tyr Arg Ile Met Arg Ser Gly Arg
    450                 455                 460

Gly Val Lys Gly Val Ser His Ala Asp Glu Leu Thr Tyr Phe Phe Trp
465                 470                 475                 480
```

```
Asn Gln Leu Ala Lys Arg Met Pro Lys Glu Ser Arg Glu Tyr Lys Thr
            485                 490                 495

Ile Glu Arg Met Thr Gly Ile Trp Ile Gln Phe Ala Thr Thr Gly Asn
            500                 505                 510

Pro Tyr Ser Asn Glu Ile Glu Gly Met Glu Asn Val Ser Trp Asp Pro
            515                 520                 525

Ile Lys Lys Ser Asp Glu Val Tyr Lys Cys Leu Asn Ile Ser Asp Glu
            530                 535                 540

Leu Lys Met Ile Asp Val Pro Glu Met Asp Lys Ile Lys Gln Trp Glu
545                 550                 555                 560

Ser Met Phe Glu Lys His Arg Asp Leu Phe
            565                 570
```

<210> SEQ ID NO 11
<211> LENGTH: 26
<212> TYPE: DNA
<213> ORGANISM: Lucilia cuprina

<400> SEQUENCE: 11
atgaatttca acgttagttt gatgga                                         26

<210> SEQ ID NO 12
<211> LENGTH: 28
<212> TYPE: DNA
<213> ORGANISM: Lucilia cuprina

<400> SEQUENCE: 12
ctaaaataaa tctctatgtt tttcaaac                                       28

<210> SEQ ID NO 13
<211> LENGTH: 570
<212> TYPE: PRT
<213> ORGANISM: Musca domestica

<400> SEQUENCE: 13

```
Met Thr Phe Leu Lys Gln Phe Ile Phe Arg Leu Lys Leu Cys Val Lys
 1               5                  10                  15

Cys Met Val Asn Lys Tyr Thr Asn Tyr Arg Leu Ser Thr Asn Glu Thr
            20                  25                  30

Gln Ile Ile Asp Thr Glu Tyr Gly Gln Ile Lys Gly Val Lys Arg Met
            35                  40                  45

Thr Val Tyr Asp Asp Ser Tyr Tyr Ser Phe Glu Ser Ile Pro Tyr Ala
        50                  55                  60

Lys Pro Pro Val Gly Glu Leu Arg Phe Lys Ala Pro Gln Arg Pro Val
65                  70                  75                  80

Pro Trp Glu Gly Val Arg Asp Cys Cys Gly Pro Ala Asn Arg Ser Val
            85                  90                  95

Gln Thr Asp Phe Ile Ser Gly Lys Pro Thr Gly Ser Glu Asp Cys Leu
            100                 105                 110

Tyr Leu Asn Val Tyr Thr Asn Asp Leu Asn Pro Asp Lys Arg Arg Pro
            115                 120                 125

Val Met Val Phe Ile His Gly Gly Asp Phe Ile Phe Gly Glu Ala Asn
            130                 135                 140

Arg Asn Trp Phe Gly Pro Asp Tyr Phe Met Lys Lys Pro Val Val Leu
145                 150                 155                 160

Val Thr Val Gln Tyr Arg Leu Gly Val Leu Gly Phe Leu Ser Leu Lys
            165                 170                 175
```

```
Ser Glu Asn Leu Asn Val Pro Gly Asn Ala Gly Leu Lys Asp Gln Val
            180                 185                 190

Met Ala Leu Arg Trp Val Lys Ser Asn Ile Ala Ile Phe Gly Gly Asp
            195                 200                 205

Val Asp Asn Ile Thr Val Phe Gly Glu Ser Ala Gly Gly Ala Ser Thr
            210                 215                 220

His Tyr Met Met Ile Thr Glu Gln Thr Arg Gly Leu Phe His Arg Gly
225                 230                 235                 240

Ile Met Met Ser Gly Asn Ser Met Cys Ser Trp Ala Ser Thr Glu Cys
                245                 250                 255

Gln Ser Arg Ala Leu Thr Met Ala Lys Arg Val Gly Tyr Lys Gly Glu
            260                 265                 270

Asp Asn Glu Lys Asp Ile Leu Glu Phe Leu Met Lys Ala Asn Pro Tyr
            275                 280                 285

Asp Leu Ile Lys Glu Glu Pro Gln Val Leu Thr Pro Glu Arg Met Gln
            290                 295                 300

Asn Lys Val Met Phe Pro Phe Gly Pro Thr Val Glu Pro Tyr Gln Thr
305                 310                 315                 320

Ala Asp Cys Val Val Pro Lys Pro Ile Arg Glu Met Val Lys Ser Ala
                325                 330                 335

Trp Gly Asn Ser Ile Pro Thr Leu Ile Gly Asn Thr Ser Tyr Glu Gly
            340                 345                 350

Leu Leu Ser Lys Ser Val Ala Lys Gln Tyr Pro Glu Val Val Lys Glu
            355                 360                 365

Leu Glu Ser Cys Val Asn Tyr Val Pro Trp Glu Leu Ala Asp Ser Glu
            370                 375                 380

Arg Ser Ala Pro Glu Thr Leu Glu Arg Ala Ala Ile Val Lys Lys Ala
385                 390                 395                 400

His Val Asp Gly Glu Thr Pro Thr Leu Asp Asn Phe Met Glu Leu Cys
                405                 410                 415

Ser Tyr Phe Tyr Phe Leu Phe Pro Met His Arg Phe Leu Gln Leu Arg
            420                 425                 430

Phe Asn His Thr Ala Gly Thr Pro Ile Tyr Leu Tyr Arg Phe Asp Phe
            435                 440                 445

Asp Ser Glu Glu Ile Ile Asn Pro Tyr Arg Ile Met Arg Phe Gly Arg
            450                 455                 460

Gly Val Lys Gly Val Ser His Ala Asp Glu Leu Thr Tyr Leu Phe Trp
465                 470                 475                 480

Asn Ile Leu Ser Lys Arg Leu Pro Lys Glu Ser Arg Glu Tyr Lys Thr
                485                 490                 495

Ile Glu Arg Met Val Gly Ile Trp Thr Glu Phe Ala Thr Thr Gly Lys
            500                 505                 510

Pro Tyr Ser Asn Asp Ile Ala Gly Met Glu Asn Leu Thr Trp Asp Pro
            515                 520                 525

Ile Lys Lys Ser Asp Asp Val Tyr Lys Cys Leu Asn Ile Gly Asp Glu
            530                 535                 540

Leu Lys Val Met Asp Leu Pro Glu Met Asp Lys Ile Lys Gln Gly Ala
545                 550                 555                 560

Ser Ile Phe Asp Lys Lys Lys Glu Leu Phe
                565                 570

<210> SEQ ID NO 14
<211> LENGTH: 1710
<212> TYPE: DNA
```

<210> ORGANISM: Musca domestica

<400> SEQUENCE: 14

```
atgactttc tgaagcaatt catatttcgc ctgaaactat gctttaaatg catggtcaat      60
aaatacacaa actaccgtct gagtacaaat gaaacccaaa taatcgatac tgaatatgga     120
caaattaagg gtgttaagcg aatgaccgtc tacgatgatt cttactacag tttcgagagt     180
atacccctatg ctaagcctcc agtgggtgag ttgagattca aggcacccca gcggcctgta    240
ccatgggagg gtgtacgtga ttgctgtggg ccagccaaca gatcggtaca gacagatttc     300
ataagtggca aacccacagg ttcggaggat tgtctatacc tgaatgtgta taccaatgac     360
ttgaacccag acaaaaggcg tcctgttatg gttttcatcc atggcggaga ttttatttc     420
ggcgaagcaa atcgtaactg gtttggtccc gactacttta tgaagaaacc cgtggtcttg    480
gtaaccgtgc aatatcgttt gggtgtgttg ggtttcctta gcctgaaatc ggaaaatctc    540
aatgtccccg gcaacgctgg cctcaaggat caagtaatgg ccttgagatg ggtcaagagt     600
aatattgcca ttttcggtgg cgatgtagac aatattaccg tcttcggcga agtgctggt     660
ggggcctcaa cccattacat gatgataacc gaacagaccc gtggtttatt ccatcgtggt    720
atcatgatgt ccgtaattc catgtgctca tgggcctcta cagaatgcca aagtcgtgcg     780
ctcaccatgg ccaaacgtgt tggctataag ggagaggaca atgaaaaaga tatcctggaa   840
ttcctaatga agccaatccc ctatgatttg atcaaagagg agccacaagt tttgacaccc    900
gaaagaatgc aaaataaggt catgtttcct tttggaccca ctgtagaacc ataccagaca    960
gccgactgtg tggtacccaa accaatcaga gaaatggtga agagcgcctg gggaaattcg   1020
atacccacat tgataggcaa tacctcctac gaaggtttgc tttccaaatc aattgccaaa   1080
caatatccgg aggttgtaaa agagttggaa tcctgtgtga attatgtgcc ttgggagttg   1140
gctgacagtg aacgcagtgc cccggaaacc ctggagaggg ctgccattgt gaaaaggcc    1200
catgtggatg gggaaacacc tactctggat aatttttatgg agctttgctc ctatttctat   1260
ttcctcttcc ccatgcatcg cttcctacaa ttgcgcttca accacacagc tggcactccc   1320
atttattgt atcgtttcga tttcgattcc gaagaaatta ttaaccccta tcgtattatg   1380
cgttttggcc gtggcgttaa aggtgtaagc catgccgatg agctaaccta tctcttctgg   1440
aacatttgt cgaaacgcct gccaaaggaa agccgcgaat acaaaaccat tgaacgcatg   1500
gttggcattt ggacggaatt cgccaccacc ggcaaaccat acagcaatga tatagccggc   1560
atggaaaacc tcacctggga tcccataaaa aaatccgatg atgtctataa atgtttaaat   1620
atcggcgatg aattgaaagt tatggatttg ccagaaatgg ataaaattaa acaatgggca   1680
agtatattcg ataaaaagaa ggaattgttt                                    1710
```

<210> SEQ ID NO 15
<211> LENGTH: 207
<212> TYPE: PRT
<213> ORGANISM: Musca domestica

<400> SEQUENCE: 15

```
Gln Thr Asp Phe Ile Ser Gly Lys Pro Thr Gly Ser Glu Asp Cys Leu
 1               5                  10                  15

Tyr Leu Asn Val Tyr Thr Asn Asp Leu Asn Pro Asp Lys Lys Arg Pro
            20                  25                  30

Val Met Val Phe Ile His Gly Gly Gly Phe Ile Phe Gly Glu Ala Asn
        35                  40                  45
```

```
Arg Asn Trp Tyr Gly Pro Asp Tyr Phe Met Lys Lys Pro Val Val Leu
        50                  55                  60
Val Thr Val Gln Tyr Arg Leu Gly Val Leu Gly Phe Leu Ser Leu Lys
 65                  70                  75                  80
Ser Glu Asn Leu Asn Val Pro Gly Asn Ala Gly Leu Lys Asp Gln Val
                 85                  90                  95
Met Ala Leu Arg Trp Phe Lys Ser Asn Ile Ala Ile Phe Gly Gly Asp
            100                 105                 110
Val Asp Asn Ile Thr Val Phe Gly Glu Ser Ala Gly Gly Ala Ser Thr
        115                 120                 125
His Tyr Met Met Ile Thr Glu Gln Thr Arg Gly Leu Phe His Arg Gly
    130                 135                 140
Ile Met Met Ser Gly Asn Ser Met Cys Ser Ser Ala Ser Thr Glu Cys
145                 150                 155                 160
Gln Ser Arg Ala Leu Thr Met Ala Lys Arg Val Gly Tyr Lys Gly Glu
                165                 170                 175
Glu Asn Glu Lys Asp Ile Leu Glu Phe Leu Met Lys Ala Asn Pro Tyr
            180                 185                 190
Asp Leu Ile Lys Glu Glu Pro Gln Val Leu Thr Pro Glu Arg Met
        195                 200                 205
```

<210> SEQ ID NO 16
<211> LENGTH: 21
<212> TYPE: DNA
<213> ORGANISM: Lucilia cuprina

<400> SEQUENCE: 16
ggatggtgtg cgtgattgtt g                                          21

<210> SEQ ID NO 17
<211> LENGTH: 21
<212> TYPE: DNA
<213> ORGANISM: Lucilia cuprina

<400> SEQUENCE: 17
aaaaggatgt ggtgttgatt a                                          21

<210> SEQ ID NO 18
<211> LENGTH: 21
<212> TYPE: DNA
<213> ORGANISM: Lucilia cuprina

<400> SEQUENCE: 18
actaatgtcg ggtaatgcta t                                          21

<210> SEQ ID NO 19
<211> LENGTH: 21
<212> TYPE: DNA
<213> ORGANISM: Lucilia cuprina

<400> SEQUENCE: 19
cactatgatg ggtaacactt c                                          21

<210> SEQ ID NO 20
<211> LENGTH: 21
<212> TYPE: DNA
<213> ORGANISM: Lucilia cuprina

<400> SEQUENCE: 20
tgttacagga gaaacaccaa c                                          21

-continued

<210> SEQ ID NO 21
<211> LENGTH: 21
<212> TYPE: DNA
<213> ORGANISM: Lucilia cuprina

<400> SEQUENCE: 21
agaatcgcgt gaatacaaaa c                                              21

<210> SEQ ID NO 22
<211> LENGTH: 21
<212> TYPE: DNA
<213> ORGANISM: Lucilia cuprina

<400> SEQUENCE: 22
acggtatacc ctcaaaactg t                                              21

<210> SEQ ID NO 23
<211> LENGTH: 21
<212> TYPE: DNA
<213> ORGANISM: Lucilia cuprina

<400> SEQUENCE: 23
tcccaaacga tattgtatgt t                                              21

<210> SEQ ID NO 24
<211> LENGTH: 21
<212> TYPE: DNA
<213> ORGANISM: Lucilia cuprina

<400> SEQUENCE: 24
acatcatgta gtgggtagaa g                                              21

<210> SEQ ID NO 25
<211> LENGTH: 21
<212> TYPE: DNA
<213> ORGANISM: Lucilia cuprina

<400> SEQUENCE: 25
ccgaggatgt ttgggtaaga c                                              21

<210> SEQ ID NO 26
<211> LENGTH: 21
<212> TYPE: DNA
<213> ORGANISM: Lucilia cuprina

<400> SEQUENCE: 26
tatcagctgt tggtgtttct c                                              21

<210> SEQ ID NO 27
<211> LENGTH: 21
<212> TYPE: DNA
<213> ORGANISM: Lucilia cuprina

<400> SEQUENCE: 27
acgcgattct ttaggcatac g                                              21

<210> SEQ ID NO 28
<211> LENGTH: 21
<212> TYPE: DNA
<213> ORGANISM: Lucilia cuprina

```
<400> SEQUENCE: 28
tgctgcctct acccactaca t                                              21

<210> SEQ ID NO 29
<211> LENGTH: 21
<212> TYPE: DNA
<213> ORGANISM: Lucilia cuprina

<400> SEQUENCE: 29
cctgtggctt ggctttcata a                                              21

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Degenerate
      Primer
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (21)
<223> OTHER INFORMATION: i
<220> FEATURE:
<221> NAME/KEY: modified_base
<222> LOCATION: (27)
<223> OTHER INFORMATION: i
<220> FEATURE:
<221> NAME/KEY: modified_base
<222> LOCATION: (30)
<223> OTHER INFORMATION: i

<400> SEQUENCE: 30
ttcgagggna tnccntaygc nmarccnccn btngg                               35

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Degenerate
      Primer
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: modified_base
<222> LOCATION: (24)
<223> OTHER INFORMATION: i
<220> FEATURE:
<221> NAME/KEY: modified_base
<222> LOCATION: (27)
<223> OTHER INFORMATION: i
```

<400> SEQUENCE: 31
acytgrtcyt tnarnccngc rttnccnggn ac         32

<210> SEQ ID NO 32
<211> LENGTH: 22
<212> TYPE: DNA
<213> ORGANISM: Musca domestica

<400> SEQUENCE: 32
tttggtcccg actactttat ga                    22

<210> SEQ ID NO 33
<211> LENGTH: 24
<212> TYPE: DNA
<213> ORGANISM: Musca domestica

<400> SEQUENCE: 33
tgccacttat gaaatctgtc tgta                  24

<210> SEQ ID NO 34
<211> LENGTH: 24
<212> TYPE: DNA
<213> ORGANISM: Musca domestica

<400> SEQUENCE: 34
tacatgatga taaccgaaca gacc                  24

<210> SEQ ID NO 35
<211> LENGTH: 23
<212> TYPE: DNA
<213> ORGANISM: Musca domestica

<400> SEQUENCE: 35
tcgattattt gggtttcatt tgt                   23

<210> SEQ ID NO 36
<211> LENGTH: 21
<212> TYPE: DNA
<213> ORGANISM: Musca domestica

<400> SEQUENCE: 36
acagacagat ttcataagtg g                     21

<210> SEQ ID NO 37
<211> LENGTH: 21
<212> TYPE: DNA
<213> ORGANISM: Musca domestica

<400> SEQUENCE: 37
tttgcattct ttcgggtgtc a                     21

<210> SEQ ID NO 38
<211> LENGTH: 21
<212> TYPE: DNA
<213> ORGANISM: Musca domestica

<400> SEQUENCE: 38
attcgatacc cacattgata g                     21

<210> SEQ ID NO 39
<211> LENGTH: 21
<212> TYPE: DNA

-continued

```
<213> ORGANISM: Musca domestica

<400> SEQUENCE: 39
ggcactccca tttatttgta t                                              21

<210> SEQ ID NO 40
<211> LENGTH: 23
<212> TYPE: DNA
<213> ORGANISM: Musca domestica

<400> SEQUENCE: 40 atgactttc tgaagcaatt cat                                             23

<210> SEQ ID NO 41
<211> LENGTH: 23
<212> TYPE: DNA
<213> ORGANISM: Musca domestica

<400> SEQUENCE: 41
aaacaattcc ttcttttat cga                                             23

<210> SEQ ID NO 42
<211> LENGTH: 21
<212> TYPE: DNA
<213> ORGANISM: Musca domestica

<400> SEQUENCE: 42
ggcatggaaa acctcacctg g                                              21

<210> SEQ ID NO 43
<211> LENGTH: 207
<212> TYPE: PRT
<213> ORGANISM: Lucilia cuprina

<400> SEQUENCE: 43
```

Gln Val Asp Phe Ile Thr Gly Lys Val Cys Gly Ser Glu Asp Cys Leu
 1               5                  10                  15

Tyr Leu Ser Val Tyr Thr Asn Asn Leu Asn Pro Glu Thr Lys Arg Pro
             20                  25                  30

Val Leu Val Tyr Ile His Gly Gly Gly Phe Ile Ile Gly Glu Asn His
         35                  40                  45

Arg Asp Met Tyr Gly Pro Asp Tyr Phe Ile Lys Lys Asp Val Val Leu
     50                  55                  60

Ile Asn Ile Gln Tyr Arg Leu Gly Ala Leu Gly Phe Leu Ser Leu Asn
 65                  70                  75                  80

Ser Glu Asp Leu Asn Val Pro Gly Asn Ala Gly Leu Lys Asp Gln Val
                 85                  90                  95

Met Ala Leu Arg Trp Ile Lys Asn Asn Cys Ala Asn Phe Gly Gly Asn
            100                 105                 110

Pro Asp Asn Ile Thr Val Phe Gly Glu Ser Ala Gly Ala Ala Ser Thr
        115                 120                 125

His Tyr Met Met Leu Thr Glu Gln Thr Arg Gly Leu Phe His Arg Gly
    130                 135                 140

Ile Leu Met Ser Gly Asn Ala Ile Cys Pro Leu Ala Asn Thr Gln Cys
145                 150                 155                 160

Gln His Arg Ala Phe Thr Leu Ala Lys Leu Ala Gly Tyr Lys Gly Glu
                165                 170                 175

-continued

```
Asp Asn Asp Lys Asp Val Leu Glu Phe Leu Met Lys Ala Lys Pro Gln
            180                 185                 190

Asp Leu Ile Lys Leu Glu Glu Lys Val Leu Thr Leu Glu Glu Arg
            195             200                 205
```